(12) United States Patent
Maeda et al.

(10) Patent No.: US 8,283,106 B2
(45) Date of Patent: Oct. 9, 2012

(54) SULFONIC ACID SALT AND DERIVATIVE THEREOF, PHOTOACID GENERATOR AGENT, AND RESIST MATERIAL AND PATTERN FORMATION METHOD USING THE PHOTOACID GENERATOR AGENT

(75) Inventors: Kazuhiko Maeda, Tokyo (JP); Yoshimi Isono, Kawagoe (JP); Satoru Narizuka, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 301 days.

(21) Appl. No.: 12/740,780

(22) PCT Filed: Oct. 31, 2008

(86) PCT No.: PCT/JP2008/069928
§ 371 (c)(1),
(2), (4) Date: Apr. 30, 2010

(87) PCT Pub. No.: WO2009/057769
PCT Pub. Date: May 7, 2009

(65) Prior Publication Data
US 2010/0304303 A1    Dec. 2, 2010

(30) Foreign Application Priority Data
Nov. 1, 2007   (JP) .................... 2007-285566

(51) Int. Cl.
*G03F 7/004*   (2006.01)
*G03F 7/30*   (2006.01)
*C07C 271/24*   (2006.01)
*C07C 309/15*   (2006.01)

(52) U.S. Cl. ............. 430/270.1; 430/326; 430/330; 430/910; 430/921; 430/922; 560/115; 562/100; 562/104; 562/105

(58) Field of Classification Search ......... 430/270.1, 430/326, 330, 907, 910, 921, 922; 560/115; 562/100, 104, 105
See application file for complete search history.

(56) References Cited

U.S. PATENT DOCUMENTS

| 2006/0228648 A1 | 10/2006 | Ohsawa et al. | |
|---|---|---|---|
| 2006/0246377 A1 | 11/2006 | Yamato et al. | |
| 2008/0085469 A1* | 4/2008 | Ohsawa et al. | 430/286.1 |
| 2009/0042114 A1 | 2/2009 | Yamato et al. | |
| 2009/0234155 A1 | 9/2009 | Oh et al. | |
| 2009/0291390 A1 | 11/2009 | Jung et al. | |
| 2010/0035185 A1 | 2/2010 | Hagiwara et al. | |
| 2010/0075256 A1 | 3/2010 | Joo et al. | |
| 2011/0015431 A1 | 1/2011 | Jodry et al. | |
| 2011/0034721 A1 | 2/2011 | Hagiwara et al. | |

FOREIGN PATENT DOCUMENTS

| CA | 2049772 A1 | 2/1992 |
|---|---|---|
| EP | 1 710 230 A1 | 10/2006 |
| JP | 4-230645 A | 8/1992 |
| JP | 2001-199955 A | 7/2001 |
| JP | 2002-214774 A | 7/2002 |
| JP | 2003-149879 A | 5/2003 |
| JP | 2004-002252 A | 1/2004 |
| JP | 2004-4561 A | 1/2004 |
| JP | 2004-242495 A | 8/2004 |
| JP | 2005-84365 A | 3/2005 |
| JP | 2006-306856 A | 11/2006 |
| JP | 2007-145797 A | 6/2007 |
| JP | 2009-7327 A | 1/2009 |
| WO | WO 02/42845 A2 | 5/2002 |
| WO | WO 2004/074242 A2 | 9/2004 |

OTHER PUBLICATIONS

International Search Report including English translation dated Dec. 2, 2008 and PCT/ISA/237 Form (Seven (7) pages).

* cited by examiner

Primary Examiner — John Chu
(74) Attorney, Agent, or Firm — Crowell & Moring LLP

(57) ABSTRACT

Disclosed is a fluorinated sulfonic acid salt or fluorinated sulfonic acid group-containing compound having a structure represented by the following general formula (A).

[Chem. 101]

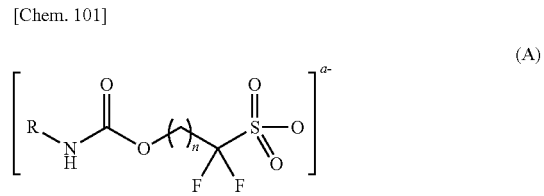

In the formula, n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; and a indicates 1 or 0. A photoacid generator containing the above fluorinated sulfonic acid salt or fluorinated sulfonic acid group-containing compound shows high sensitivity to an ArF excimer laser or the like, presents no concerns about human body accumulation, can generate an acid (photoacid) of sufficiently high acidity, and exhibits high solubility in a resist solvent and good compatibility with a resist resin.

21 Claims, No Drawings

SULFONIC ACID SALT AND DERIVATIVE THEREOF, PHOTOACID GENERATOR AGENT, AND RESIST MATERIAL AND PATTERN FORMATION METHOD USING THE PHOTOACID GENERATOR AGENT

TECHNICAL FIELD

The present invention relates to a novel sulfonic acid salt and a derivative thereof suitably usable as photoacid generators for resist materials, a photoacid generator, a resist material using the photoacid generator, and a pattern formation method.

BACKGROUND ART

In recent years, there has been a rapid advance toward finer pattern rules for high integration and high speed performance of LSI devices. The application of shorter-wavelength exposure light sources is seen as one factor behind the advance toward finer pattern rules. For example, the wavelength reduction from a mercury lamp i line (365 nm) to a KrF excimer laser (248 nm) enables mass production of 64-Mbit DRAM (Dynamic Random Access Memory) (with a processing size of 0.25 µm or smaller). The application of lithography process using an ArF excimer laser (193 nm) has also been thoroughly studied to produce DRAM with an integration of 256M and 1G or higher. In particular, the combination of the ArF lithography process with a high NA lens (NA≧0.9) is being studied for production of 65-nm node devices. For production of next 45-nm node devices, a $F_2$ laser of 157 nm wavelength is considered as a candidate for use in lithography process. However, the application of the $F_2$ lithography process has been postponed due to many problems such as increase in scanner cost, change of optical system and low resist etch resistance. As an alternative to the $F_2$ lithography process, ArF immersion lithography process has been proposed. Development is currently proceeding for early introduction of the ArF immersion lithography process.

As resists suitable for use in such an exposure wavelength range, attention is being given to "chemically amplified resist materials". The chemically amplified resist material is a pattern forming material that contains a radiosensitive acid generator (hereinafter referred to as "photoacid generator"), which is capable of generating an acid by irradiation of a radiation (hereinafter referred to as "exposure"), and forms a pattern by making a difference in developer solubility between exposed and unexposed portions through a reaction using the acid generated by exposure as a catalyst.

Various researches have been made on photoacid generators for use in chemically amplified resist materials. Conventionally, a chemically amplified resist material for exposure to a KrF excimer laser uses a photoacid generator that generates an alkane- or arene-sulfonic acid. It is however known that the use of such a photoacid generator in an ArF chemically amplified resist material does not cause a sufficient acidity for cleavage of an acid labile group of the resist resin and thereby results in resolution failure or low resist sensitivity so that the resist material cannot be suitable for device production.

For this reason, the ArF chemically amplified resist material generally uses a photoacid generator that generates a perfluoroalkanesulfonic acid of high acidity such as a perfluorooctanesulfonic acid, or a derivative thereof, known by its acronym "PFOS". There have however been discussed problems about the stability (non-degradability) of PFOS due to C—F bonds as well as the biological concentration and accumulation of PFOS due to hydrophobic and lipophilic natures. The above problems start being raised to perfluoroalkanesulfonic acids having a carbon number of 5 or more.

In order to cope with these PFOS-related problems, the development of partially fluorinated alkanesulfonic acids of lower fluorine substitution degree has been pursued by manufacturers. For example, Patent Document 1 describes the development of α,α-difluoroalkanesulfonic acid salt from α,α-difluoroalkene and a sulfur compound and discloses a resist material containing such a sulfonic acid salt, e.g., di(4-tert-butylphenyl)iodonium 1,1-difluoro-2-(1-naphthyl)ethanesulfonate, as a photoacid generator to generate a corresponding sulfonic acid by exposure. Patent Document 2 describes the development of α,α,β,β-tetrafluoroalkanesulfonic acid salt from α,α,β,β-tetrafluoro-α-iodoalkane and a sulfur compound and a photoacid generator using this sulfonic acid salt as a photoacid generator to generate a corresponding sulfonic acid and a resist composition containing the photoacid generator. Patent Document 3 discloses a photoacid generator having a difluorosulfoacetic acid alkyl ester (e.g. 1-(alkoxycarbonyl)-1,1-difluoromethanesulfonate), a difluorosulfoacetic acid amide (e.g. 1-carbamoyl-1,1-difluoromethanesulfonate) or the like although there is no mention made on the synthesis method of this photoacid generator. Further, Patent Document 4 discloses triphenylsulfonium (adamantan-1-ylmethyl)oxycarbonyldifluoromethanesulfonate although there is no mention made on the synthesis example of this sulfonate compound. Patent Document 5 discloses a triphenylsulfonium alkyloxycarbonyldifluoromethanesulfonate having a lactone structure etc. Furthermore, Patent Document 6 discloses triphenylsulfonium 2-acyloxy-1,1,3,3,3-hexafluoropropanesulfonate etc.

Patent Document 1: Japanese Patent Application Publication No. 2004-531749
Patent Document 2: Japanese Laid-Open Patent Publication No. 2004-2252
Patent Document 3: Japanese Laid-Open Patent Publication No. 2002-214774
Patent Document 4: Japanese Laid-Open Patent Publication No. 2004-4561
Patent Document 5: Japanese Laid-Open Patent Publication No. 2006-306856
Patent Document 6: European Patent Application Publication No. 1710230A1

DISCLOSURE OF THE INVENTION

For the purpose of fine pattern line width control, it is important that the chemically amplified resist material has not only high resolution performance but also the capability of forming a resist film with good flatness after the resist patterning. The chemically amplified resist material, if inferior in film surface flatness, leads to a deterioration of pattern dimension system as a result of transfer of surface roughness conditions (nano edge roughness) of the resist film at the time of transferring a resist pattern to the substrate by etching treatment etc. This finally results in a loss of device electrical characteristics.

In order for the resist film to attain good flatness, it is also necessary to disperse the photoacid generator uniformly in the chemically amplified resist material. The resist solvent solubility and resin compatibility of the photoacid generator are thus considered as very important factors.

However, any of the conventional photoacid generators derived from the partially fluorinated alkanesulfonic acids does not have satisfactory solvent solubility and resin compatibility so that the resulting resist film fails to obtain a high level of surface flatness due to an insufficient amount of the photoacid generator dissolved in the resist material.

The present invention has been made in consideration of the above circumstances. It is an object of the present invention to provide a photoacid generator (sulfonic acid onium salt) that shows high sensitivity to a high-energy radiation such as ultraviolet ray, far-ultraviolet ray, extreme-ultraviolet ray, electron beam, X-ray, excimer laser, γ-ray or synchrotron radiation, notably ArF excimer laser, and good substrate adhesion and etching resistance characteristics, has no concern about accumulation in human body, can generate an acid (photoacid) having a sufficiently high acidity, an appropriate boiling point and an appropriately short diffusion length within a resist film, and exhibits high solubility in a resist solvent and good compatibility with a resist resin and to provide a resist material containing such a photoacid generator. It is also an object of the present invention to provide a pattern formation method for forming a good pattern shape with the use of such a resist material.

There are various requirements for an acid generated from a photoacid generator. For example, it is required that the acid generated from the photoacid generator have a sufficient acidity, appropriate dispersibility in the resist material, a sufficiently high boiling point and less volatility, be less likely to be eluted in water, be decomposed without environmental load, and dissolve well in a resist solvent and resin. Among others, the acidity and environmental load of the acid, the solubility of the acid in the resist solvent and the compatibility of the acid with the resist resin are particularly important issues. It has heretofore been difficult to simultaneously control all of the acidity, environmental load, resist solvent solubility and resin compatibility of the acid. More specifically, there is a problem that the environmental load such as biological concentration and accumulation of the acid becomes increased as the acid increases in acidity with fluorine content. There is also a problem that the resist solvent solubility and resin compatibility of the acid becomes decreased when a large substituent group is introduced to the acid so as to control the diffusion length of the acid in the resist film. In this way, the acid generated from the conventional photoacid generator has not reached a point where it can satisfy all of the above requirements.

As a result of extensive researches made to overcome the above problems, the present inventors have found a fluorinated sulfonic acid salt or fluorinated sulfonic acid group-containing compound having a structure represented by the following general formula (A).

[Chem. 1]

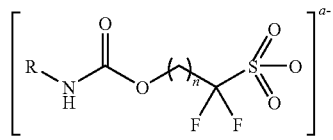

(A)

In the formula, n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; and a indicates 1 or 0.

In the case of a=1, the moiety inside the parentheses of the general formula (A) constitutes a monovalent anion as a whole and forms "a fluorinated sulfonic acid salt" as the entire chemical species by combination with a counter cation. In the case of a=0, the oxygen atom (—O) on the right side of the general formula (A) has a single bond to another atom to thereby form "a fluorinated sulfonic acid group-containing compound" as the entire chemical species.

In particular, it has been found that a fluorinated sulfonic acid of the following general formula (2) is a sufficiently strong acid and is useful for resist pattern formation even though the fluorine content of the fluorinated sulfonic acid is relatively low.

[Chem. 2]

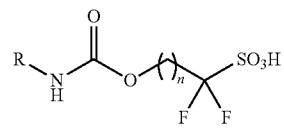

(2)

In the formula, n indicates an integer of 1 to 10; and R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group.

It has further been found that: a precursor compound (referred to as "photoacid generator") capable of generating the above fluorinated sulfonic acid by exposure exhibits much better compatibility with a resist material (base resin/resist solvent) than those of conventional compounds so that the use of such a photoacid generator compound enables higher-resolution resist pattern than conventional ones. It has also been found that the thus-formed resist pattern shows good performance such as substrate adhesion and etching resistance.

The most remarkable characteristics of the fluorinated sulfonic acid of the general formula (2) is that the fluorinated sulfonic acid has two fluorine atoms on the α-position carbon of the sulfonic acid group, and at the same time, has a urethane moiety on the side opposite from the sulfonic acid group. The acidity of the sulfonic acid group significantly increases due to the direct bonding of the two fluorine atoms to the α-position carbon of the sulfonic acid group and does not become impaired by the urethane bond of the molecule. As a result, there can be provided the photoacid generator that contains less fluorine atoms and allows a significant reduction of environmental load.

It has further been found that it is possible to significantly improve the solubility of the precursor compound (photoacid generator) to the resist solvent and the compatibility of the precursor compound (photoacid generator) with the base resin by introducing the urethane bond into the basic carbon-chain skeleton of the molecule. The use of a resist material containing such a photoacid generator enables higher-resolution resist pattern formation.

The above precursor compound (photoacid generator) can preferably be a fluorinated sulfonic acid onium salt represented by the following general formula (3), a fluorinated N-sulfonyloxyimide compound represented by the following general formula (4) and a fluorinated oxime sulfonate compound represented by the following general formula (5), each of which shows high sensitivity to exposure to a high-energy radiation such as ultraviolet ray, far-ultraviolet ray, extreme-ultraviolet ray, electron beam, X-ray, excimer laser, γ-ray or synchrotron radiation (notably, excimer laser).

[Chem. 3]

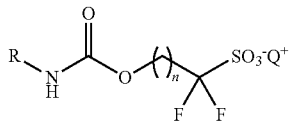
(3)

In the formula, n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; and $Q^+$ indicates a sulfonium cation of the following general formula (a) or the following general formula (b) or a iodonium cation of the following general formula (c).

[Chem. 4]

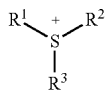
(a)

In the general formula (a), $R^1$, $R^2$ and $R^3$ each independently indicate a substituted or unsubstituted $C_1$-$C_{10}$ linear or branched alkyl, alkenyl or oxoalkyl group, or a substituted or unsubstituted $C_6$-$C_{18}$ aryl, aralkyl or aryloxoalkyl group. Two or more of $R^1$, $R^2$ and $R^3$ may be bonded to each other to form a ring structure with a sulfur atom in the formula.

[Chem. 5]

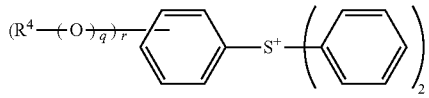
(b)

In the general formula (b), $R^4$ indicates a substituted or unsubstituted $C_1$-$C_{20}$ linear, branched or cyclic alkyl or alkenyl group, or a substituted or unsubstituted $C_6$-$C_{14}$ aryl group; r indicates an integer of 1 to 5; and q indicates 0 or 1.

[Chem. 6]

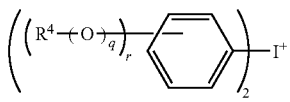
(c)

In the general formula (c), $R^4$ indicates a substituted or unsubstituted $C_1$-$C_{20}$ linear, branched or cyclic alkyl or alkenyl group, or a substituted or unsubstituted $C_6$-$C_{14}$ aryl group; r indicates an integer of 1 to 5; and q indicates 0 or 1.

[Chem. 7]

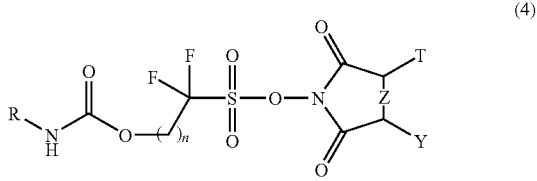
(4)

In the general formula (4), n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; Z indicates a single bond, a double bond, a methylene group or an oxygen atom; T and Y each independently indicate a hydrogen atom or a substituted or unsubstituted $C_1$-$C_{10}$ alkyl group; and T and Y may form an aliphatic cyclic structure, an aromatic ring structure or a heterocyclic structure in cooperation with each other and with carbon atoms bonded thereto.

[Chem. 8]

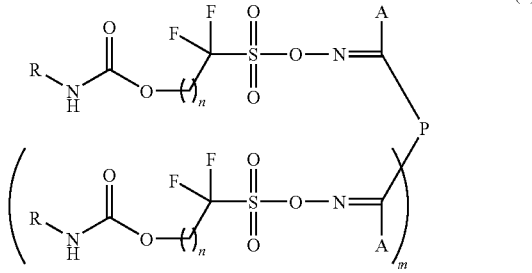
(5)

In the general formula (5), n each independently indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; m indicates 0 or 1; p indicates a substituted or unsubstituted $C_1$-$C_{20}$ alkyl group or a substituted or unsubstituted $C_6$-$C_{15}$ aryl group in the case of m=0 and indicates a single bond, a substituted or unsubstituted $C_1$-$C_{20}$ alkylene group or a substituted or unsubstituted $C_6$-$C_{15}$ arylene group in the case of m=1; A indicates a cyano group, a trifluoromethyl group, a perfluoroethyl group, a perfluoropropyl group, a 5H-perfluoropentyl group, a 6H-perfluorohexyl group, a nitro group or a methyl group; and, in the case of m=1, both of A may be bonded to each other to form a six-carbon ring with carbon atoms bonded thereto.

The present inventors have previously found a fluorinated sulfonic acid onium salt of the following general formula (B) and a corresponding sulfonic group-containing compound (neutral molecule) each containing less fluorine atoms, but having the function of generating a strong acid and showing good compatibility with a solvent or resin so that these materials are useful as acid generators for resin materials, and have already filed patent applications (Japanese Patent Application No. 2007-143879 and No. 2007-143880) based on such findings (cf. Reference Examples 1 and 2 mentioned later).

[Chem. 9]

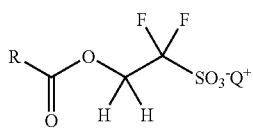

(B)

In the general formula (B), R is the same as that of the present invention.

The photoacid generator of the present invention corresponds to that in which "an ester bond" on the left side of the above material is replaced with "a urethane bond", so as to achieve better compatibility with the solvent or resin while maintaining the basic advantages of the above inventions.

The most remarkable characteristic of the photoacid generator of the present invention is that the photoacid generator has not only a urethane bond but also two fluorine substituents (F) on the α-position carbon of the sulfonic acid salt. In the present invention, the urethane moiety is located at one end of the sulfonic acid onium salt so that it is possible to introduce a urethane moiety of different structure, as needed, in the presence of a corresponding isocyanate and thereby freely control the performance characteristics of the photoacid generator. More specifically, the boiling point of the photoacid generator can be controlled appropriately by the introduction of a high-molecular-weight urethane or a bulky urethane moiety. The resist solvent solubility and resin compatibility of the photoacid generator can be improved arbitrarily by the introduction of a highly fat-soluble urethane moiety. It is also feasible to introduce a urethane moiety having a double bond at an end thereof so that, in some cases, the photoacid generator can be dispersed in the base resin by copolymerization with another resist monomer. This allows an improvement in the resist solvent solubility of the photoacid generator and contributes to the solutions of the above-mentioned problems.

Moreover, the present inventors have found, as a suitable common raw material for the above photoacid generator compounds, a fluorinated sulfonic acid salt represented by the following general formula (1).

[Chem. 10]

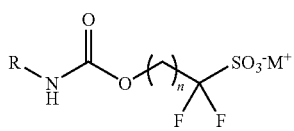

(1)

In the formula, n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; and $M^+$ indicates a lithium ion, a sodium ion, a potassium ion, an ammonium ion or a tetramethylammonium ion.

The present inventors have also found a resist material (composition) formed by combination of any of the above photoacid generator compounds with a solvent and a specific base resin.

In connection with the above findings, the present inventors have found a method for preparing the fluorinated sulfonic acid of the general formula (2) and a resist pattern forming method. The present invention has been accomplished based on these findings.

According to the present invention, there is provided a fluorinated sulfonic acid salt or fluorinated sulfonic acid group-containing compound having a structure represented by the following general formula (A).

[Chem. 11]

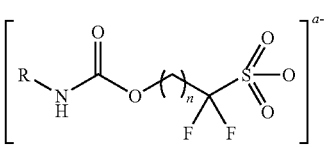

(A)

(In the formula, n, R and a are the same as defined above.)

There is also provided according to the present invention a fluorinated sulfonic acid onium salt represented by the following general formula (3).

[Chem. 12]

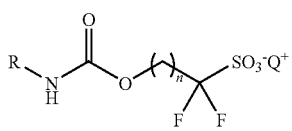

(3)

(In the formula, n, R and $Q^+$ are the same as defined above.)

There is provided according to the present invention a fluorinated N-sulfonyloxyimide compound represented by the following general formula (4).

[Chem. 13]

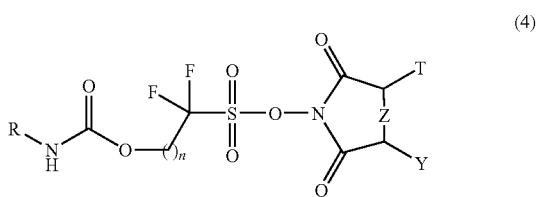

(4)

(In the formula, n, R, Z, T and Y are the same as defined above.)

There is provided according to the present invention a fluorinated oxime sulfonate compound represented by the following general formula (5).

[Chem. 14]

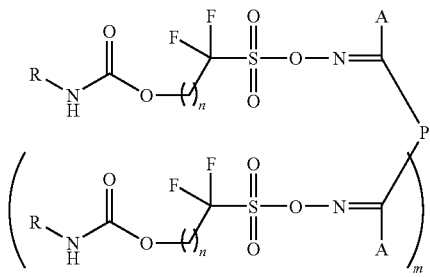

(5)

(In the formula, N, R, m, p and A are the same as defined above.)

There is provided according to the present invention a fluorinated sulfonic acid salt represented by the following general formula (1).

[Chem. 15]

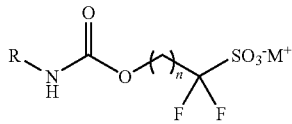

(1)

(In the formula, n, R and M$^+$ are the same as defined above.)

There is provided according to the present invention a first photoacid generator for a chemically amplified resist material, which is sensitive to a high-energy radiation selected from ultraviolet ray, far-ultraviolet ray, extreme-ultraviolet ray, electron beam, X-ray, excimer laser, γ-ray and synchrotron radiation and is capable of generating a fluorinated sulfonic acid of the following general formula (2) by exposure to the high-energy radiation.

[Chem. 16]

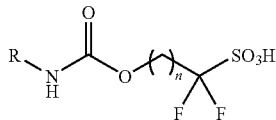

(2)

(In the formula, n and R are the same as defined above.)

There is provided according to the present invention a second photoacid generator for a chemically amplified resist material, which is sensitive to a high-energy radiation selected from ultraviolet ray, far-ultraviolet ray, extreme-ultraviolet ray, electron beam, X-ray, excimer laser, γ-ray and synchrotron radiation and contains at least one of the above fluorinated sulfonic acid onium salt, fluorinated N-sulfonyloxyimide compound and fluorinated oxime sulfonate compound.

There is further provided a method for generating the fluorinated sulfonic acid of the general formula (2), including the step of irradiating the second photoacid generator with a high-energy radiation selected from ultraviolet ray, far-ultraviolet ray, extreme-ultraviolet ray, electron beam, X-ray, excimer laser, γ-ray and synchrotron radiation.

According to the present invention, there is provided a first resist material containing a base resin, a photoacid generator and a solvent, wherein the photoacid generator is capable of generating the fluorinated sulfonic acid of the general formula (2).

There is also provided according to the present invention a second resist material containing a base resin, a photoacid generator and a solvent, wherein the photoacid generator is the second photoacid generator.

The first or second resist material may be a third resist material in which the base resin is either a polymer of one kind of monomer, or a copolymer of two or more kinds of monomers, selected from the group consisting of olefins, fluoroolefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers.

The first or second resist material may be a fourth resist material in which the base resin is a polymer compound having a repeating unit represented by the following general formula (6).

[Chem. 17]

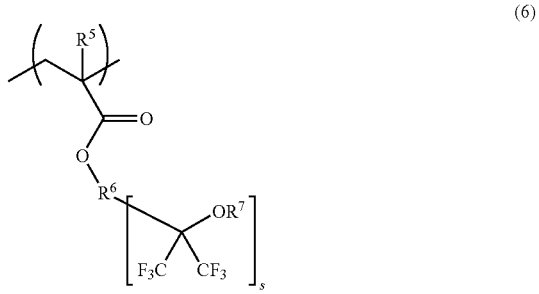

(6)

In the formula (6), R$^5$ indicates a hydrogen atom, a halogen atom, a hydrocarbon group or a fluoroalkyl group; R$^6$ indicates a linear or branched alkyl group, an alkyl group having a ring structure, an aromatic ring, or a composite group thereof, and may partially be fluorinated; R$^7$ indicates a hydrogen atom, a hydrocarbon group that may be branched, a fluoroalkyl group, or a cyclic group having an aromatic structure or aliphatic ring structure, and may contain an oxygen or carbonyl bond; and s indicates an integer of 1 to 2.

The fourth resist material may be a fifth resist material in which the repeating unit of the base resin is represented by the following general formula (7).

[Chem. 18]

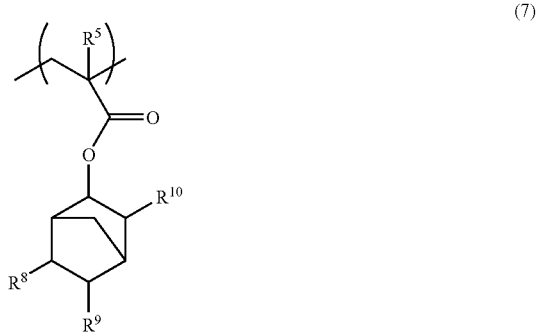

(7)

In the formula (7), R$^5$ indicates a hydrogen atom, a halogen atom, a hydrocarbon group, or a C$_1$-C$_3$ alkyl or fluoroalkyl group; either one of R$^8$, R$^9$ and R$^{10}$ indicates a CF$_3$C(CF$_3$)(OH)CH$_2$— group and the other two of R$^8$, R$^9$ and R$^{10}$ indicate hydrogen atoms.

The fourth resin material may be a sixth resin material in which the repeating unit of the base resin is represented by the following general formula (8).

[Chem. 19]

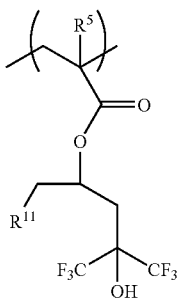
(8)

In the formula (8), $R^3$ indicates a hydrogen atom, a halogen atom, a hydrocarbon group or a fluoroalkyl group; and $R^{11}$ indicates a hydrogen atom, a methyl group, an ethyl group, a n-propyl group, an isopropyl group, a n-butyl group, a sec-butyl group, a tert-butyl group, a fluoromethyl group, a difluoromethyl group, a trifluoromethyl group or a perfluoroethyl group.

The fourth resist material may be a seventh resist material in which the repeating unit of the base resin is represented by the following general formula (9).

[Chem. 20]

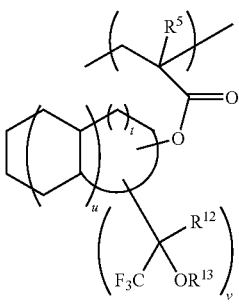
(9)

In the formula (9), $R^5$ indicates a hydrogen atom, a halogen atom, a hydrocarbon group or a fluoroalkyl group; $R^{12}$ indicates a methyl group or a trifluoromethyl group; $R^{13}$ indicates a hydrogen atom, a $C_1$-$C_{25}$ linear or $C_3$-$C_{25}$ branched or cyclic hydrocarbon group, or a $C_6$-$C_{26}$ aromatic hydrocarbon group, a part of which may contain a fluorine atom, an oxygen atom or a carbonyl bond; u indicates an arbitrary integer of 0 to 2; t and v each independently indicate an arbitrary integer of 1 to 8 and satisfy a relationship of $v \leq t+2$; and, when there are a plurality of $R^{12}$ and $R^{13}$, they may be the same or different.

The first or second resist material may be an eighth resist material in which the base resin contains a repeating unit represented by the following general formula (10).

[Chem. 21]

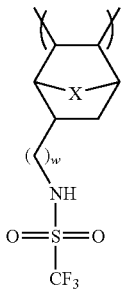
(10)

In the general formula (10), X indicates either —$CH_2$—, —O— or —S—; and w indicates an integer of 2 to 6.

The first or second resist material may be a ninth resist material in which the base resin contains a repeating unit represented by the following general formula (11).

[Chem. 22]

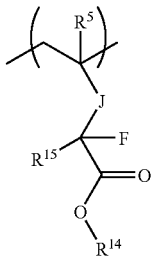
(11)

In the general formula (11), $R^3$ indicates a hydrogen atom, a halogen atom, a hydrocarbon group or a fluoroalkyl group; $R^{15}$ indicates a fluorine atom or a fluoroalkyl group; J indicates a divalent linking group; and $R^{14}$ indicates an acid-labile protecting group represented by either one of the following general formulas (d) to (h).

[Chem. 23]

$$R^{16}\text{—O—C}(=\text{O})\text{—} \quad (d)$$

In the general formula (d), $R^{16}$ indicates a $C_1$-$C_4$ alkyl group that may have a substituent, a $C_3$-$C_{30}$ alicyclic hydrocarbon group that may have a substituent, or a $C_6$-$C_{14}$ aryl group that may have a substituent.

[Chem. 24]

$$R^{16}\text{—O—CHR}^{17}\text{—} \quad (e)$$

In the general formula (e), $R^{16}$ is the same as defined in the general formula (d); $R^{17}$ indicates a hydrogen atom, a $C_1$-$C_4$ alkyl group that may have a substituent, a $C_3$-$C_{30}$ alicyclic hydrocarbon group that may have a substituent, a $C_1$-$C_6$ alkoxy group that may have a substituent, a $C_2$-$C_4$ alkenyl group that may have a substituent, a $C_6$-$C_{14}$ aryl group that may have a substituent, or a $C_7$-$C_{20}$ aralkyl group that may have a substituent.

[Chem. 25]

$$CR^{18}R^{19}R^{20}\text{—} \quad (f)$$

In the general formula (f), $R^{18}$, $R^{19}$ and $R^{20}$ may be the same or different and each independently indicate a $C_1$-$C_4$ alkyl group that may have a substituent, a $C_3$-$C_{30}$ alicyclic hydrocarbon group that may have a substituent, a $C_2$-$C_4$ alkenyl group that may have a substituent, a $C_6$-$C_{14}$ aryl group that may have a substituent, or a $C_7$-$C_{20}$ aralkyl group that may have a substituent; and two of $R^{18}$, $R^{19}$ and $R^{20}$ may be bonded to each other to form a ring structure.

[Chem. 26]

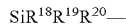
(g)

In the general formula (g), $R^{18}$, $R^{19}$ and $R^{20}$ are the same as defined in the general formula (f).

[Chem. 27]

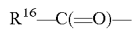
(h)

In the general formula (h), $R^{16}$ is the same as defined in the general formula (d).

Either of the first to ninth resist materials may be a chemically amplified resist material (tenth resist material) in which the base resin is insoluble or difficult to dissolve in a developer and is made soluble in the developer by the action of an acid.

According to the present invention, there is provided a pattern formation method (first method) including the steps of: applying one of the first to tenth resist materials to a substrate; after heat treating the applied resist material, exposing the applied resist material to a high-energy radiation of 300 nm or less wavelength through a photomask; and, after heat treating the exposed resist material as needed, developing the exposed resist material with a developer.

The first method may be a pattern formation method (second method) performed by immersion lithography using an ArF excimer laser of 193 nm wavelength as the high energy radiation and allowing insertion of water, or a liquid of higher refractive index than that of the air, between the substrate and projector lens.

According to the present invention, there is also provided triphenylsulfonium cyclohexylcarbamic acid-2,2-difluoroethylsulfonate.

According to the present invention, there is further provided triphenylsulfonium adamantane-1-yl-carbamic acid-2,2-difluoroethylsulfonate.

DETAILED DESCRIPTION

A sulfonic acid onium salt of the present invention has less fear of biological concentration and accumulation because of a low fluorine atom content in its molecular structure and has the capability of generating an acid of sufficiently high acidity by exposure. This sulfonic acid onium salt, when used as a photoacid generator in a resist material, shows high sensitivity to an ArF excimer laser and exhibits good surface adhesion and etching resistance characteristics. Further, the photoacid generator (sulfonic acid onium salt) can be provided with good resist solvent solubility and resin compatibility by the introduction of an urethane bond in the molecular structure. There can be provided a resist material containing such a photoacid generator and a pattern formation method capable of forming a good pattern shape with the use of such a resist material. The present invention benefits from the above excellent effects.

Hereinafter, preferred embodiments of the present invention will be described in detail below. It should be understood that the present invention is not limited to the following embodiments and that various changes and modifications can be made to the following embodiments, without departing from the scope of the present invention, based on the general knowledge of a person skilled in the art.

[Fluorinated Sulfonic Acid Salt]

A fluorinated sulfonic acid, which is useful as a common raw material of the photoacid generator compounds of the present invention, is represented by the following general formula (1).

[Chem. 28]

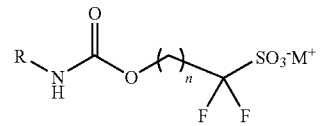
(1)

In the formula, n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; $M^+$ indicates a lithium ion, a sodium ion, a potassium ion, an ammonium ion or a tetramethylammonium ion.

A substituent on R of the general formula (1) can be a $C_1$-$C_{20}$ linear, branched or cyclic alkoxy group, a halogen atom (a fluorine atom, a chlorine atom, a iodine atom), a cyano group, a hydroxy group, a carboxyl group, a $C_1$-$C_{20}$ linear, branched or cyclic alkoxycarbonyl group, a $C_1$-$C_{20}$ linear, branched or cyclic alkylcarbonyloxy group, a lactone group, an amino group, an amide group or the like.

Specific examples of R of the general formula (1) are methyl, ethyl, n-propyl, isopropyl, cyclopropyl, n-butyl, sec-butyl, isobutyl, tert-butyl, n-pentyl, cyclopentyl, n-hexyl, 2-ethylhexyl, cyclohexyl, n-octyl, n-decyl, n-dodecyl, 1-adamantyl, 2-adamantyl, bicyclo[2.2.1]heptene-2-yl, 1-adamantanemethyl, 2-adamantanemethyl, phenyl, 4-methoxyphenyl, 4-tert-butylphenyl, 4-biphenyl, 1-naphthyl, 2-naphthyl, 10-anthranyl and 2-furanyl. As the substituent, there can be used alkyl substituents each having a polymerizable group e.g. an acryloyloxy group or methacryloyloxy group, such as 2-methacryloyloxyethyl, 2-acryloyloxyethyl and 1,1-bis(acryloylmethyl)ethyl. Other examples of the substituent are those containing a carbonyl group, a lactone group and a hydroxyl group as indicated below.

[Chem. 29]

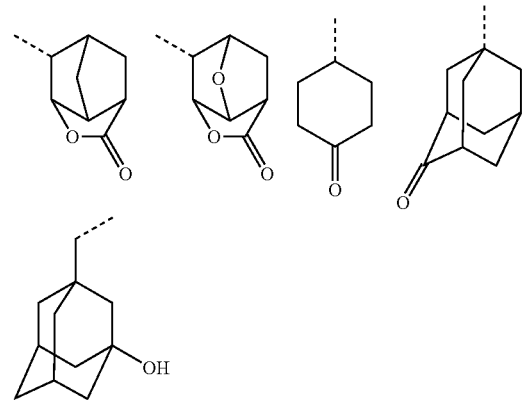

(In the formula, the dotted line indicates a bonding position.)

In the general formula (1), the lithium ion, sodium ion, potassium ion, ammonium ion or tetramethylammonium ion is employed as $M^+$ in view of the ease of preparation of the sulfonic acid salt and the ease of separation of the sulfonic acid. Any other cation such as a calcium ion or a magnesium ion may alternatively be employed without particular limitation as long as the sulfonic acid exists stably.

In the case of using the fluorinated sulfonic acid salt as a raw material of the after-described photoacid generator, R and n correspond to those of the photoacid generator.

[Photoacid Generators]

A photoacid generator of the present invention is typified by a fluorinated onium salt, a fluorinated oxime sulfonate or a fluorinated sulfonyloxyimide, each of which can be derived from the above fluorinated sulfonic acid salt. This photoacid generator is sensitive to a high-energy radiation such as ultraviolet ray, far-ultraviolet ray, extreme-ultraviolet ray, electron beam, X-ray, excimer laser, γ-ray or synchrotron radiation to generate a fluorinated sulfonic acid of the following general formula (2) by exposure to such a high-energy radiation and is thus useful for use in a chemically amplified resist material.

[Chem. 30]

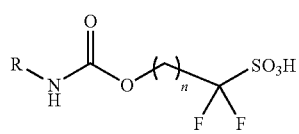

(2)

In the formula, n indicates an integer of 1 to 10; and R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group.

Herein, R and n in the general formula (2) are the same as those defined in the general formula (1).

Specific examples of the fluorinated sulfonic acid of the general formula (2) are indicated below.

[Chem. 31]

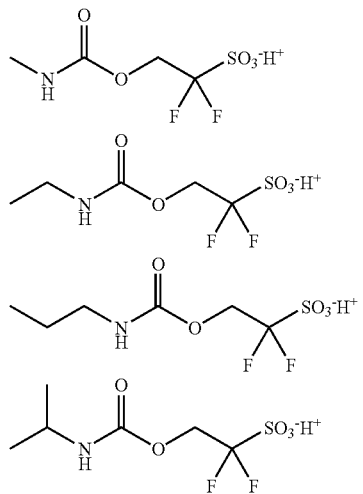

-continued

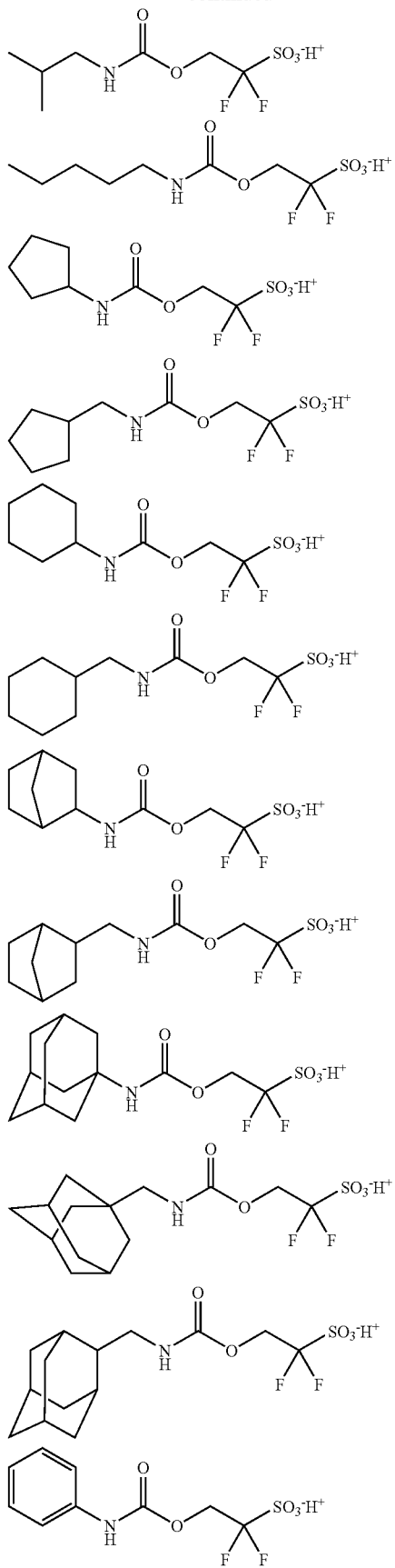

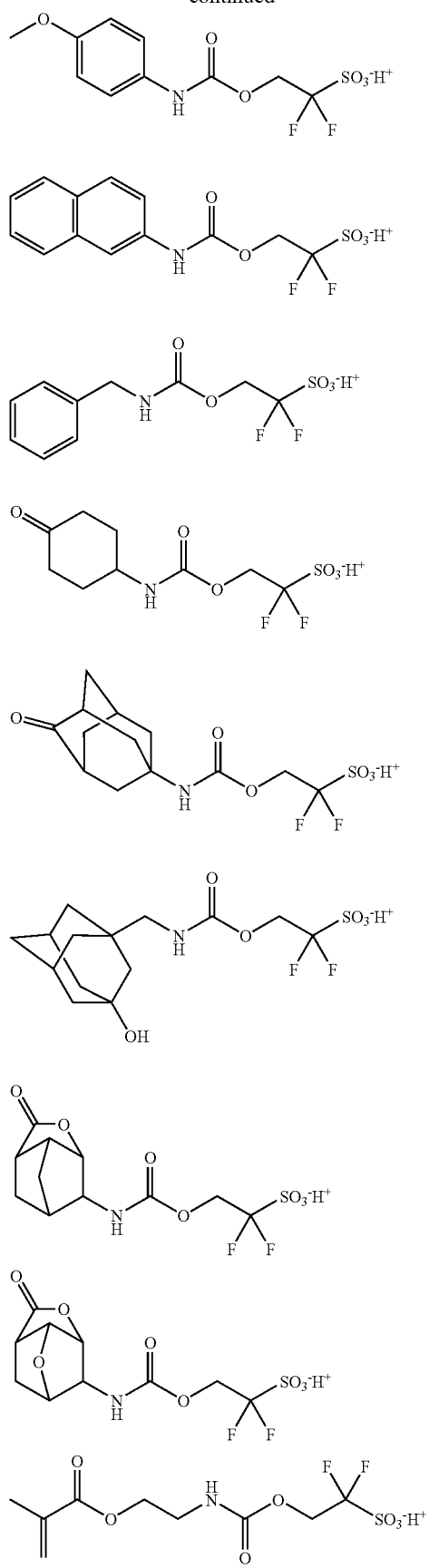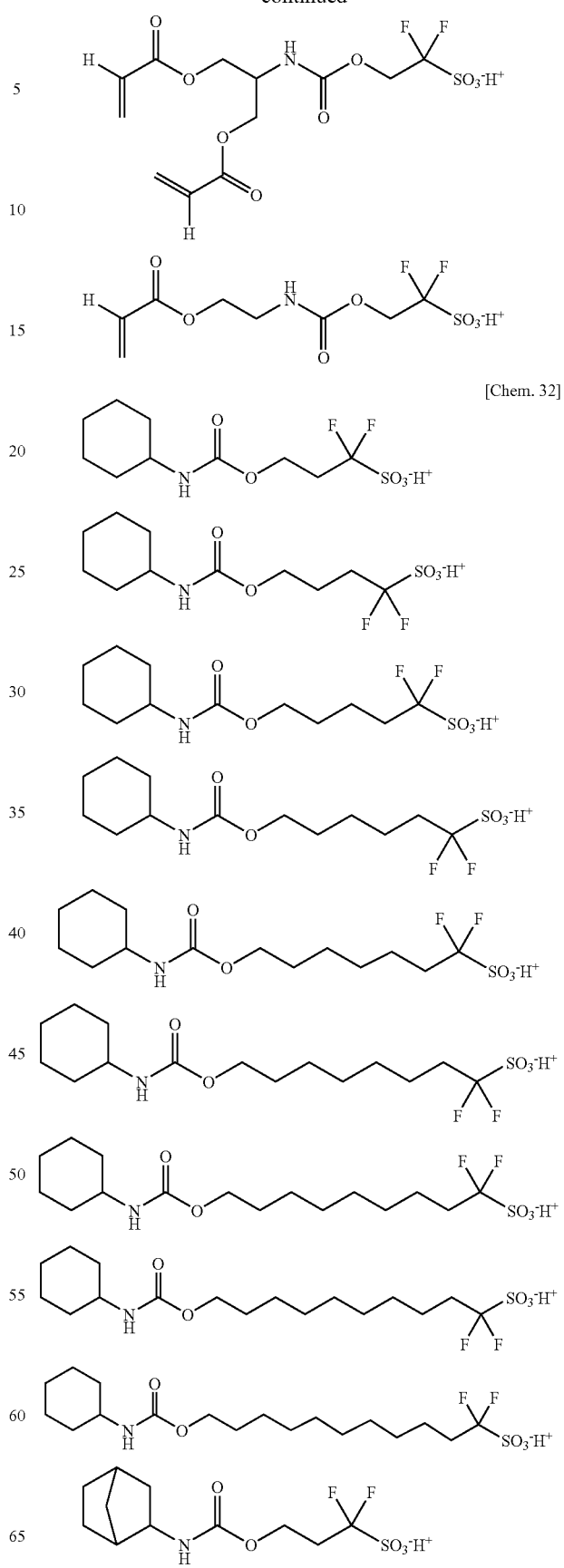

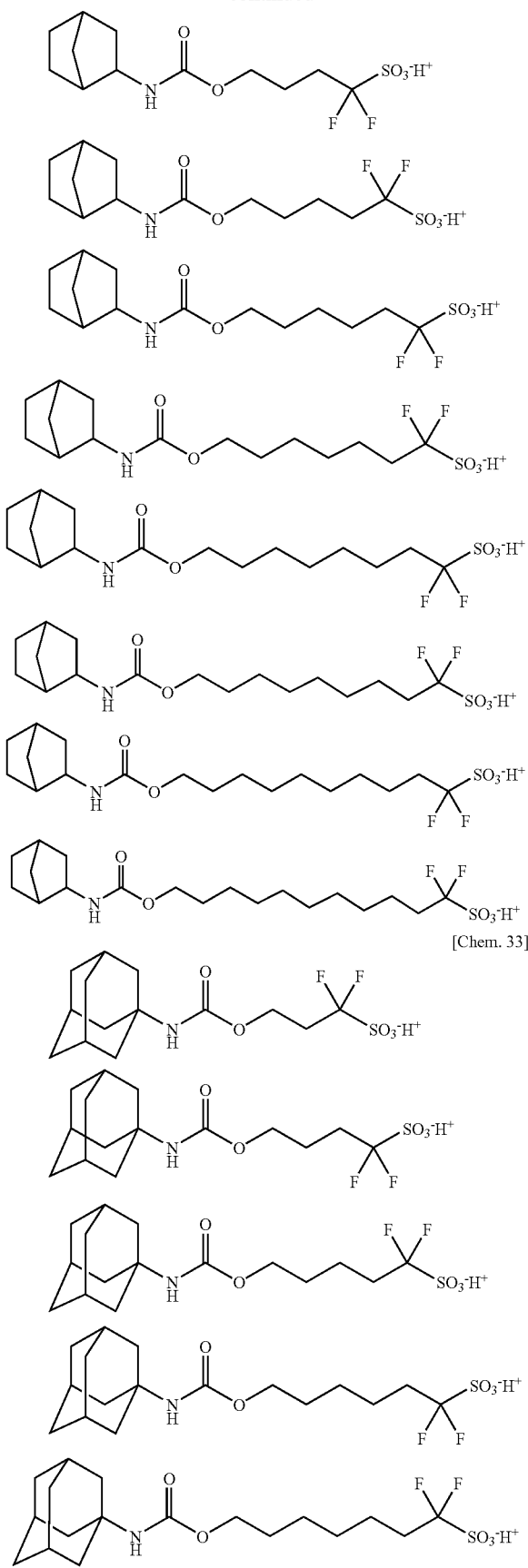

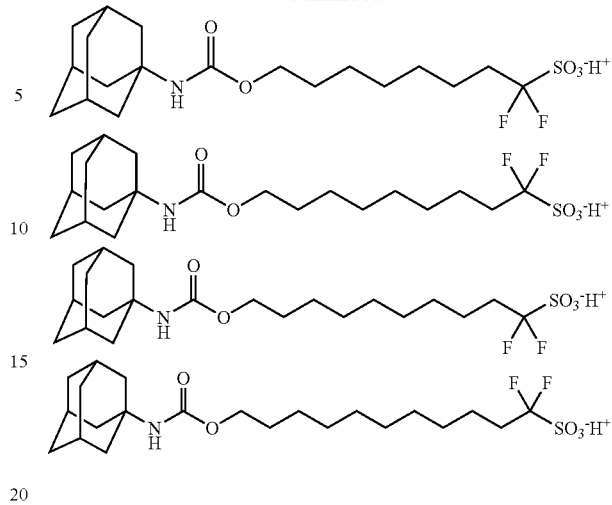

Among others, n is preferably 1 to 4, particularly preferably 1 in view of the boiling point, diffusion length and ease of preparation. Further, R is particularly preferably cyclohexyl, 2-norbornyl or 1-adamantyl. In other words, the following fluorinated sulfonic acids are particularly preferred.

[Chem. 34]

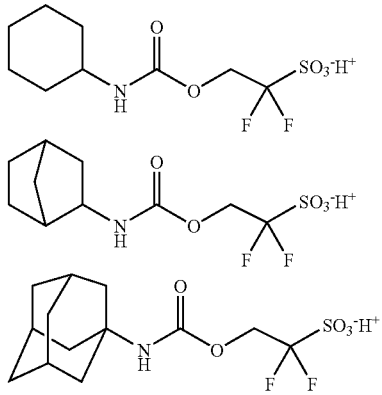

[Fluorinated Sulfonic Acid Onium Salt]

The fluorinated sulfonic acid onium salt of the present invention is represented by the following general formula (3).

[Chem. 35]

(3)

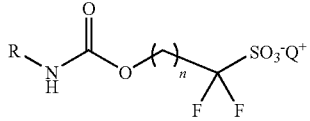

In the formula, n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group.

Further, $Q^+$ indicates either a sulfonium cation of the following general formula (a) or the following general formula (b) or a iodonium cation of the following general formula (c).

[Chem. 36]

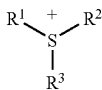
(a)

In the general formula (a), $R^1$, $R^2$ and $R^3$ each independently indicate a substituted or unsubstituted $C_1$-$C_{10}$ linear or branched alkyl, alkenyl or oxoalkyl group, or a substituted or unsubstituted $C_6$-$C_{18}$ aryl, aralkyl or aryloxoalkyl group. Two or more of $R^1$, $R^2$ and $R^3$ may be bonded to each other to form a ring structure with a sulfur atom in the formula.

[Chem. 37]

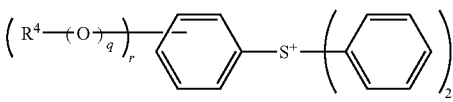
(b)

In the general formula (b), $R^4$ indicates a substituted or unsubstituted $C_1$-$C_{20}$ linear, branched or cyclic alkyl or alkenyl group, or a substituted or unsubstituted $C_6$-$C_{14}$ aryl group; r indicates an integer of 1 to 5; and q indicates 0 or 1.

[Chem. 38]

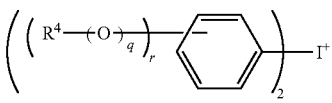
(c)

In the general formula (c), $R^4$ indicates a substituted or unsubstituted $C_1$-$C_{20}$ linear, branched or cyclic alkyl or alkenyl group, or a substituted or unsubstituted $C_6$-$C_{14}$ aryl group; r indicates an integer of 1 to 5; and q indicates 0 or 1.

The sulfonium cations of the general formulas (a) and (b) and the iodonium cation of the general formula (c) will be explained in detail below.

Sulfonium Cation of General Formula (a)

Examples of $R^1$, $R^2$ and $R^3$ in the general formula (a) are as follows: alkyl groups such as methyl, ethyl, n-propyl, isopropyl, cyclopropyl, n-butyl, sec-butyl, isobutyl, tert-butyl, n-pentyl, cyclopentyl, n-hexyl, n-heptyl, 2-ethylhexyl, cyclohexyl, cycloheptyl, 4-methylcyclohexyl, cyclohexylmethyl, n-octyl, n-decyl, 1-adamantyl, 2-adamantyl, bicyclo[2.2.1]heptene-2-yl, 1-adamantanemethyl and 2-adamantanemethyl; alkenyl groups such as vinyl, allyl, propenyl, butenyl, hexenyl and cyclohexenyl; oxoalkyl groups such as 2-oxocyclopentyl, 2-oxocyclohexyl, 2-oxopropyl, 2-oxoethyl, 2-cyclopentyl-2-oxoethyl, 2-cyclohexyl-2-oxoethyl and 2-(4-methylcyclohexyl)-2-oxoethyl; aryl groups such as phenyl, naphthyl, thienyl, alkoxyphenyl e.g. p-methoxyphenyl, m-methoxyphenyl, o-methoxyphenyl, p-ethoxyphenyl, p-tert-butoxyphenyl or m-tert-butoxyphenyl, alkylphenyl e.g. 2-methylphenyl, 3-methylphenyl, 4-methylphenyl or ethylphenyl, alkylnaphthyl e.g. methylnaphthyl or ethylnaphthyl, dialkylnaphthyl e.g. diethylnaphthyl and dialkoxynaphthyl e.g. dimethoxynaphthyl or diethoxynaphthyl; aralkyl groups such as benzyl, 1-phenylethyl and 2-phenylethyl; and aryloxoalkyl groups such as 2-aryl-2-oxoethyl e.g. 2-phenyl-2-oxoethyl, 2-(1-naphthyl)-2-oxoethyl and 2-(2-naphthyl)-2-oxoethyl. In the case where two or more of $R^1$, $R^2$ and $R^3$ are bonded to each other to form a ring structure with a sulfur atom in the molecule, there can be used 1,4-butylene, 3-oxa-1,5-pentylene and the like. There can also be used an aryl group having a polymerizable substituent e.g. as acryloyloxy or methacryloyloxy, such as 4-(acryloyloxy)phenyl, 4-(methacryloyloxy)phenyl, 4-vinyloxyphenyl, 4-vinylphenyl and the like.

Specific examples of the sulfonium cation of the general formula (a) are triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-buthylphenyl)sulfonium, (3,4-di-tert-butylphenyl)diphenylsulfonium, bis(3,4-di-tert-butylphenyl)phenylsulfonium, tris(3,4-di-tert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tent-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl 2-thienylsulfonium, 4-n-butoxynaphthyl-1-thiacyclopentanium, 2-n-butoxynaphthyl-1-thiacyclopentanium, 4-methoxynaphthyl-1-thiacyclopentanium and 2-methoxynaphthyl-1-thiacyclopentanium. Among others, preferred are triphenylsulfonium, (4-tert-buthylphenyl)diphenylsulfonium, (4-tert-butoxyphenyl)diphenylsulfonium, tris(4-tert-butylphenyl)sulfonium and (4-tert-butoxycarbonylmethyloxyphenyl)diphenylsulfonium and the like.

There can also be used 4-(methacryloyloxy)phenyldiphenylsulfonium, 4-(acryloyloxy)phenyldiphenylsulfonium, 4-(methacryloyloxyl)phenyldimethylsulfonium, 4-(acryloyloxy)phenyldimethylsulfonium and the like. These polymerizable sulfonium cations can be prepared with reference to Japanese Laid-Open Patent Publication No. 4-230645, Japanese Laid-Open Patent Publication No. 2005-84365 and the like.

Sulfonium Cation of General Formula (b)

There is no particular limitation on the position of $R^4$—$(O)_q$— substituent in the general formula (b). The $R^4$—$(O)_q$— substituent is preferably located at the 4- or 3-position, more preferably the 4-position, of the phenyl group. Herein, q is 0 or 1. Examples of $R^4$ are methyl, ethyl, n-propyl, sec-propyl, cyclopropyl, n-butyl, sec-butyl, isobutyl, tert-butyl, n-pentyl, cyclopentyl, n-hexyl, cyclohexyl, n-octyl, n-decyl, n-dodecyl, 1-adamantyl, 2-adamantyl, bicyclo[2.2.1]heptene-2-yl, phenyl, 4-methoxyphenyl, 4-tert-butylphenyl, 4-biphenyl, 1-naphthyl, 2-naphthyl, 10-anthranyl and 2-furanyl. In the case of q=1, acryloyl, methacryloyl, vinyl and allyl are also usable.

Specific examples of the sulfonium cation of the general formula (b) are (4-methylphenyl)diphenylsulfonium, (4-ethylphenyl)diphenylsulfonium, (4-cyclohexylphenyl)diphenylsulfonium, (4-n-hexylphenyl)diphenylsulfonium, (4-n-octylphenyl)diphenylsulfonium, (4-methoxyphenyl)diphenylsulfonium, (4-ethoxyphenyl)diphenylsulfonium, (4-tert-butoxyphenyl)diphenylsulfonium, (4-cyclohexyloxyphenyl)diphenylsulfonium, (4-trifluoromethylphenyl)diphenylsulfonium, (4-trifluoromethyloxyphenyl)diphenylsulfonium and (4-tert-butoxycarbonylmethyloxyphenyl)diphenylsulfonium.

Iodonium Cation of General Formula (c)

There is no particular limitation on the position of $R^4$—$(O)_q$— substituent in the general formula (c). The $R^4$—$(O)_q$— substituent is preferably located at the 4- or 3-position, more preferably the 4-position, of the phenyl group. Herein, q is 0 or 1. Examples of $R^4$ in the general formula (c) are the same as those in the general formula (b).

Specific examples of the iodonium cation of the general formula (c) are bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium and (4-methacryloyloxy)phenylphenyliodonium. Among others, bis(4-tert-butylphenyl)iodonium is preferred.

The sulfonic acid salt of the general formula (1) and the sulfonic acid onium salt of the general formula (3) can be prepared by e.g. a method indicated by the following scheme 1.

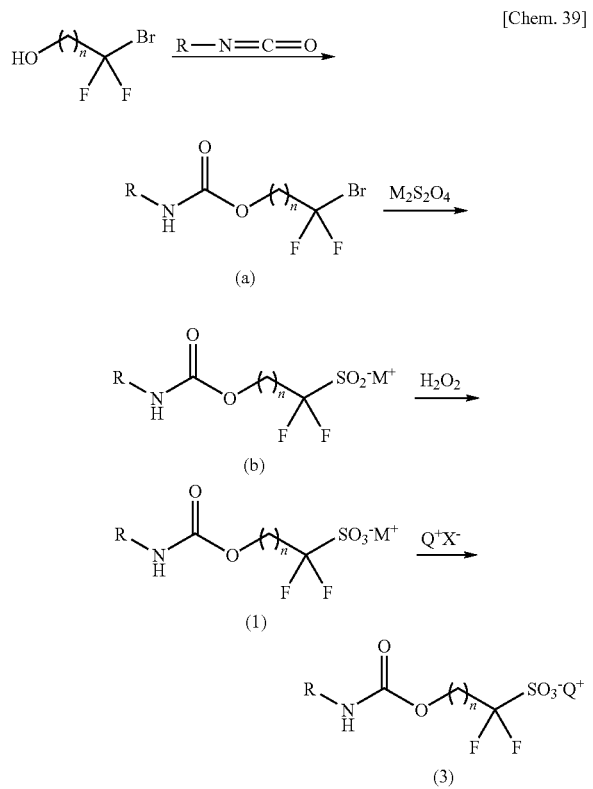

In the scheme 1, R and n are the same as defined in the general formula (1) and in the general formula (3); $Q^+$ is the same as defined in the general formula (3); M of $M_2S_2O_4$ indicates lithium, sodium, potassium, ammonium or tetramethylammonium; and $X^-$ indicates a monovalent anion.

Namely, the preparation method includes the following four steps.

First step: forming a fluorine-containing bromo urethane (carbamate) of the general formula (a) by reaction of ω-bromo-ω,ω-difluoroalkanol and isocyanate.

Second step: forming a fluorine-containing sulfinate compound of the general formula (b) by sulfination of the fluorine-containing bromo urethane (carbamate) of the general formula (a) formed in the first step with a sulfinating agent such as dithionite.

Third step: forming the fluorinated sulfonic acid salt of the general formula (1) by oxidation of the fluorine-containing sulfinate compound of the general formula (b) formed in the second step with an oxidizing agent such as hydrogen peroxide.

Fourth step: forming the fluorinated sulfonic acid onium salt of the general formula (3) by reaction of the fluorinated sulfonic acid salt of the general formula (1) formed in the third step with a univalent onium salt $Q^+X^-$.

In the fluorinated sulfonium acid onium salt, n is preferably 1 to 4 (particularly preferably 1); and R is particularly preferably cyclohexyl, 2-norbornyl or 1-adamantyl, as in the case of the fluorinated sulfonic acid generated by exposure. In this case, $Q^+$ is preferably triphenylsulfonium ion, (4-tert-butylphenyl)diphenylsulfonium ion, (4-tert-butoxyphenyl)diphenylsulfonium ion, tris(4-tert-butylphenyl)sulfonium ion, (4-tert-butoxycarbonylmethyloxyphenyl)diphenylsulfonium ion or bis(4-tert-butylphenyl)iodonium ion. Particularly preferred is triphenylsulfonium ion. Accordingly, preferred examples of the fluorinated sulfonic acid onium salt are triphenylsulfonium cyclohexylcarbamic acid-2,2-difluoroethylsulfonate, triphenylsulfonium 2-norbornylcarbamic acid-2,2-difluoroethylsulfonate and triphenylsulfonium adamantane-1-yl-carbamic acid-2,2-difluoroethylsulfonate. In other words, the following fluorinated sulfonic acid onium salts are particularly preferred.

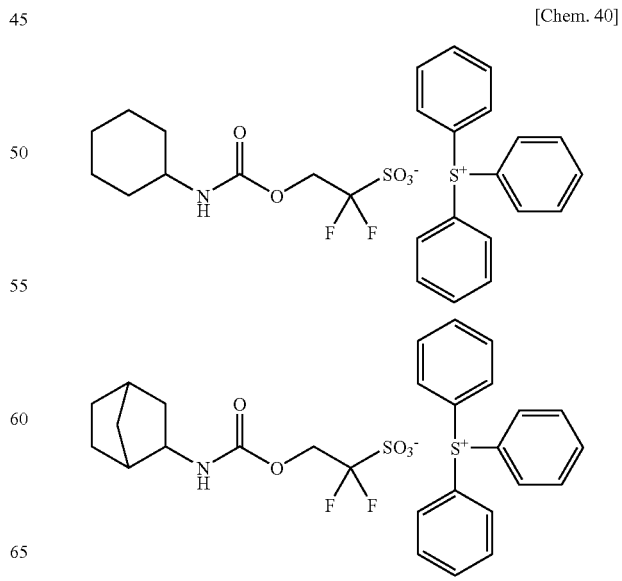

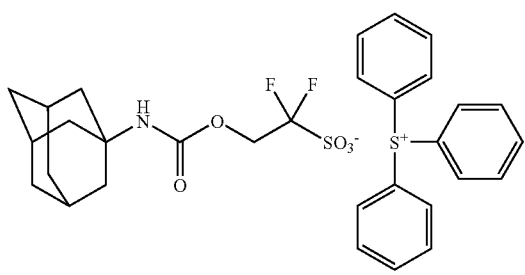

[Fluorinated N-Sulfonyloxyimide Compound]

The fluorinated N-sulfonyloxyimide compound of the present invention is represented by the following general formula (4).

[Chem. 41]

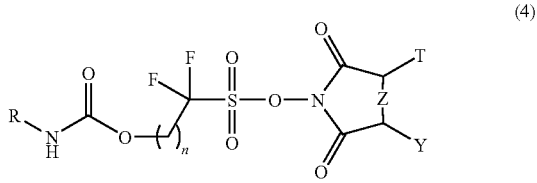

(4)

In the general formula (4), n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_5$-$C_{15}$ aryl group, or a $C_4$-$C_{15}$ heteroaryl group; Z indicates a single bond, a double bond, a methylene group or an oxygen atom; T and Y each independently indicate a hydrogen atom or a substituted or unsubstituted $C_1$-$C_{10}$ alkyl group; and T and Y may form an aliphatic cyclic structure, an aromatic ring structure or a heterocyclic structure in cooperation with each other and with carbon atoms bonded thereto.

Examples of R are the same as indicated above. Examples of the aliphatic cyclic structure, aromatic ring structure and heterocyclic structure formed by T and Y in cooperation with the carbon atoms bonded thereto (i.e. the right-side moiety of the general formula (4)) are those indicated below.

[Chem. 42]

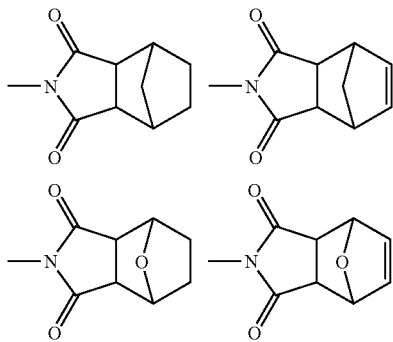

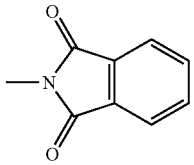

The preparation method of the fluorinated N-sulfonyloxyimide compound of the general formula (4) will be next explained below. This compound can be prepared with reference to Japanese Laid-Open Patent Publication No. 2001-199955 and the like. More specifically, the sulfonic acid salt of the general formula (1) is first converted to a sulfonyl chloride by treatment with phosphorous pentachloride, thionyl chloride, phosphorus oxychloride etc.

The sulfonyl chloride is then reacted with a N-hydroxydicarboxylmide of the general formula (1), which is commercially available or prepared from a corresponding dicarboxylic acid and hydroxylamine, under basic conditions by dissolution thereof in a solvent such as THF, dichloromethane etc., or in a basic solvent such as triethylamine, pyridine etc.

[Chem. 43]

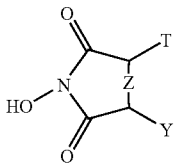

(i)

In the formula, Z indicates a single bond, a double bond, a methylene group or an oxygen atom; T and Y each independently indicates a hydrogen atom or a substituted or unsubstituted $C_1$-$C_{10}$ alkyl group; and T and Y may form an aliphatic cyclic structure, an aromatic ring structure or a heterocyclic structure in cooperation with each other and with carbon atoms bonded thereto.

With this, the target fluorinated N-sulfonyloxyimide compound of the general formula (4) is obtained (cf. the following scheme 2).

[Scheme 2]

[Chem. 44]

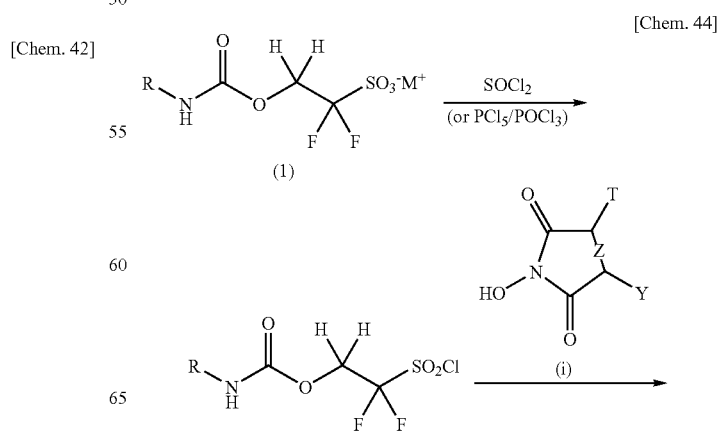

-continued

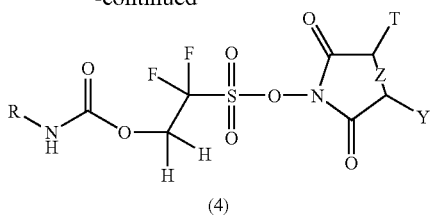

(4)

In the fluorinated N-sulfonyloxyimide compound, preferred n and R are the same as those in the fluorinated sulfonic acid onium salt. In this case, the following structures are preferred as the right-side moiety of the formula (4).

[Chem. 45]

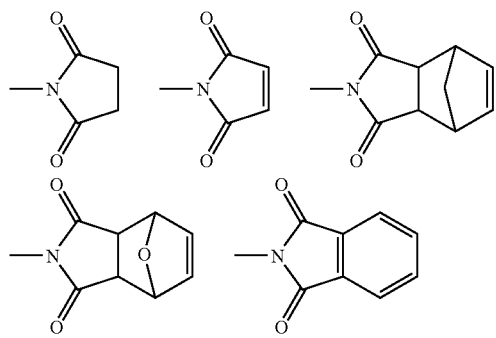

[Fluorinated Oxime Sulfonate Compound]

The fluorinated oxime sulfonate compound of the present invention is represented by the following general formula (5).

[Chem. 46]

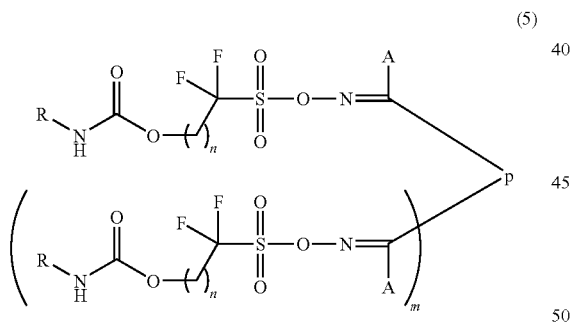

(5)

In the general formula (5), n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; in indicates 0 or 1; p indicates a substituted or unsubstituted $C_1$-$C_{20}$ alkyl group or a substituted or unsubstituted $C_6$-$C_{15}$ aryl group in the case of m=0 and indicates a single bond, a substituted or unsubstituted $C_1$-$C_{20}$ alkylene group or a substituted or unsubstituted $C_6$-$C_{15}$ arylene group in the case of m=1; A indicates a cyano group, a trifluoromethyl group, a perfluoroethyl group, a perfluoropropyl group, a 5H-perfluoropentyl group, a 6H-perfluorohexyl group, a nitro group or a methyl group; and, in the case of m=1, both of A may be bonded to each other to form a six-carbon ring with carbon atoms bonded thereto.

Examples of R are the same as indicated above. The skeleton of the oxime sulfonate compound can be set with reference to e.g. International Patent Publication No. 2004/074242.

Examples of the skeleton of the oxime sulfonate compound, except its sulfonic acid moiety, are indicated below.

[Chem. 47]

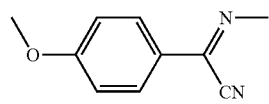

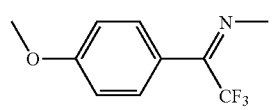

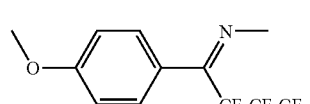

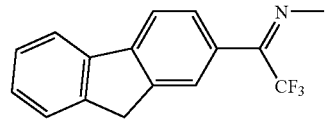

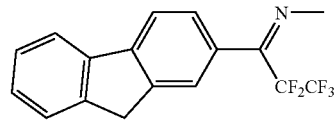

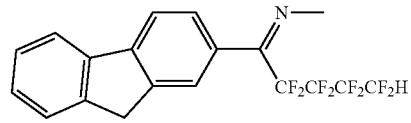

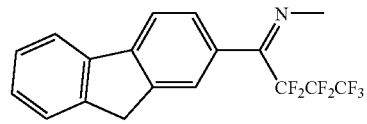

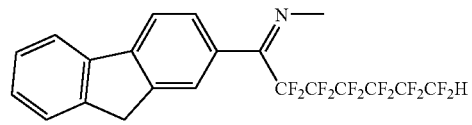

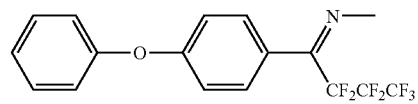

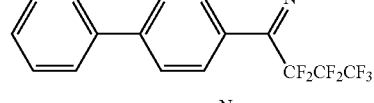

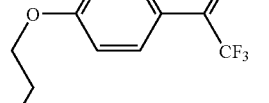

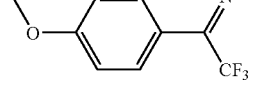

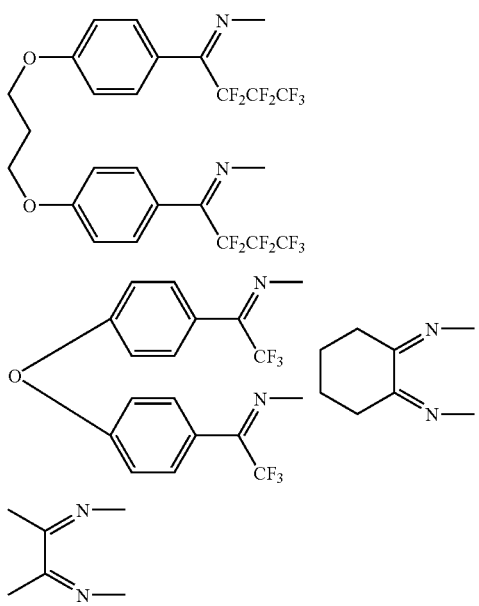

The preparation method of the oxime sulfonate compound of the general formula (5) will be next explained below. This compound can also be prepared with reference to the above-mentioned patent document and the like. More specifically, the sulfonic acid salt of the general formula (1) is first converted to a sulfonyl chloride by treatment with phosphorous pentachloride, thionyl chloride, phosphorus oxychloride etc.

The sulfonyl chloride is then reacted with an oxime of the general formula (ii), which is commercially available or prepared from a corresponding ketone and hydroxylamine, under basic conditions by dissolution in a solvent such as THF, dichloromethane etc., or in a basic solvent such as triethyl amine, pyridine etc.

[Chem. 48]

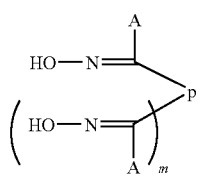

(ii)

In the formula, in indicates 0 or 1; p indicates a substituted or unsubstituted $C_1$-$C_{20}$ alkyl group or a substituted or unsubstituted $C_6$-$C_{15}$ aryl group in the case of m=0 and indicates a single bond, a substituted or unsubstituted $C_1$-$C_{20}$ alkylene group or a substituted or unsubstituted $C_6$-$C_{15}$ arylene group in the case of n=1; A indicates a cyano group, a trifluoromethyl group, a perfluoroethyl group, a perfluoropropyl group, a 5H-perfluoropentyl group, a 6H-perfluorohexyl group, a nitro group or a methyl group; and, in the case of n=1, both of A may be bonded to each other to form a six-carbon ring with carbon atoms bonded thereto.

With this, the target oxime sulfonate compound of the general formula (5) is obtained (cf. the following scheme 3).

[Scheme 3]

[Chem. 49]

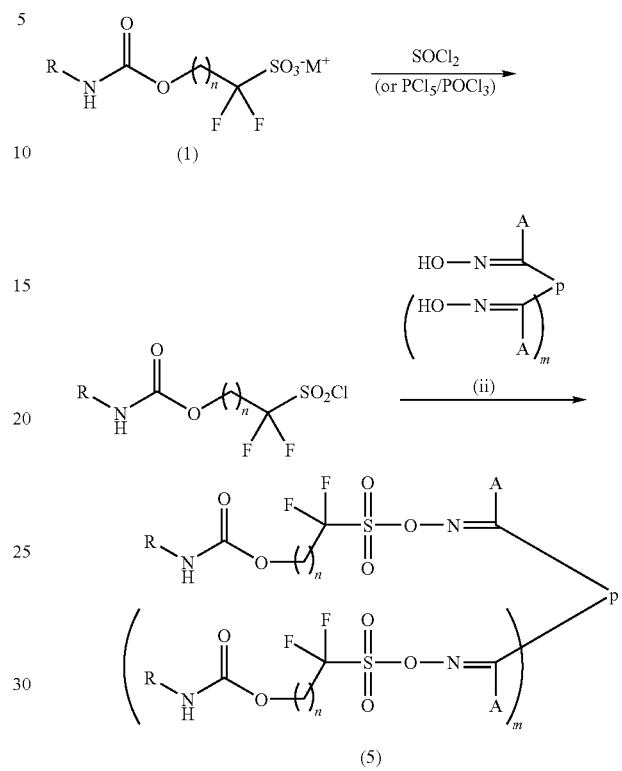

In the fluorinated oxime sulfonate compound, preferred n and R are the same as those in the fluorinated sulfonic acid onium salt. In this case, A is preferably a cyano group or a trifluoromethyl group; and in is preferably 0. In the case of in m=0, the following structures are preferred as p.

[Chem. 50]

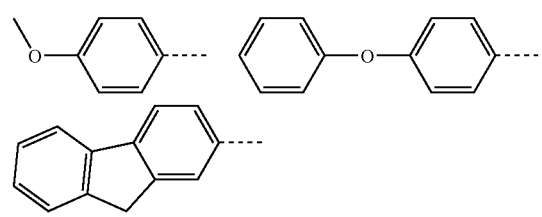

(In the formula, the dotted line indicates a bonding position.)

[Photoacid Generator of Chemically Amplified Resist Material]

As described above, the fluorinated sulfonic acid of the general formula (2) according to the present invention can be generated by irradiating either the fluorinated sulfonic acid onium salt of the general formula (3), the fluorinated N-sulfonyloxyimide compound of the general formula (4) or the fluorinated oxime sulfonate compound of the general formula (5) with a high-energy radiation such as ultraviolet ray, far-ultraviolet ray, extreme-ultraviolet ray, electron beam, X-ray, excimer laser, γ-ray or synchrotron radiation (cf. the following scheme 4).

[Scheme 4]

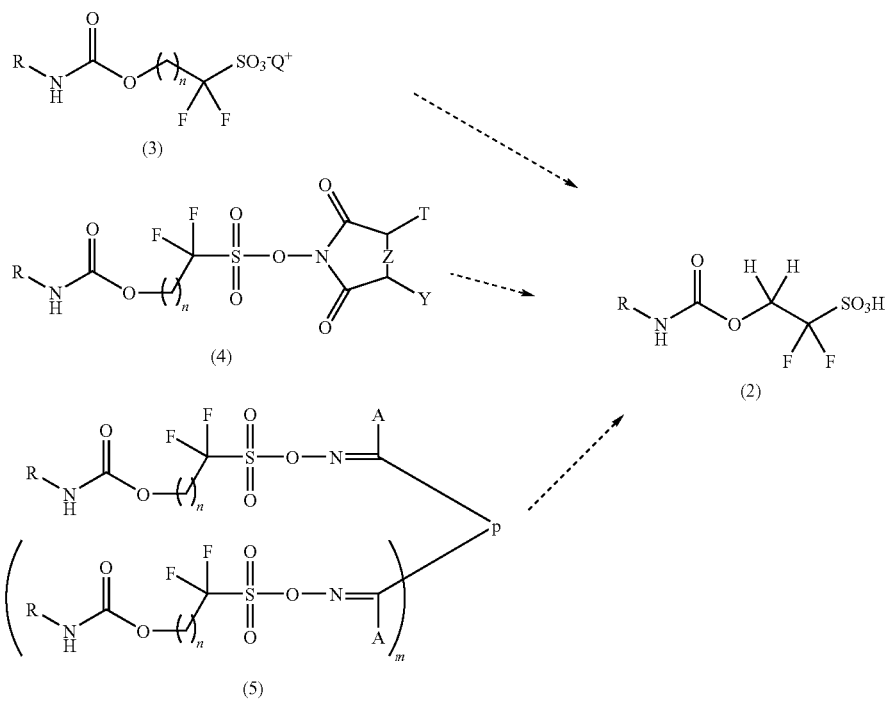

Accordingly, either of the fluorinated sulfonic acid onium salt of the general formula (3), the fluorinated N-sulfonyloxyimide compound of the general formula (4) and the fluorinated oxime sulfonate compound of the general formula (5) can be used as the photoacid generator.

The photoacid generator of the present invention thus contains either of the fluorinated sulfonic acid onium salt of the general formula (3), the fluorinated N-sulfonyloxyimide compound of the general formula (4) and the fluorinated oxime sulfonate compound of the general formula (5) as an active component. The photoacid generator of the present invention is used, by mixing with a resin (referred to as "photosensitive resin") capable of changing its solubility in an alkaline developer by the action of an acid, to form a photosensitive resin composition (resist material). (In general, the fluorinated sulfonic acid onium salt is mixed alone (in solid form) or together with another photoacid generator into the photosensitive resin.)

This resin composition has a wide range of uses as photosensitive compositions. One use of the resin composition is as a positive resist composition in which, when the photoacid generator of the present invention generates an strong acid (fluorinated sulfonic acid of the general formula (2)) by irradiation of a light or active energy ray, the resin gets transformed to a polymer having an acidic, developer-soluble unit such as a carboxylic acid, phenol or hexafluoroalcohol moiety due to the elimination of a protecting group from a side chain of the resin by the action of the generated strong acid. Another use of the resin composition is as a negative resist composition in which, when the photoacid generator of the present invention generates an strong acid by irradiation of a light or active energy ray, the resin becomes insoluble in a developer due to the reaction of a functional group on a side change of the resin with a previously mixed cross-linking agent by the action of the generated strong acid.

Next, the resist material of the present invention will be explained in detail below. The resist material of the present invention contains a base resin, a photoacid generator, a solvent, and optionally an additive such as a basic compound, a dissolution inhibitor, a cross-linking agent and the like.

The photoacid generator of the resist material is as described above. The content of the photoacid generator in the resist material is preferably 0.1 to 15 parts by weight, more preferably 1 to 10 parts by weight, per 100 parts by weight of the base resin.

[Base Resin]

The base resin of the resist material will be explained below. Preferably, the base resin has a repeating unit with no aromatic substituent. The base resin can suitably be a polymer of one kind of monomer, or a copolymer of two or more kinds of monomers, selected from the group consisting of olefins, fluoroolefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers.

Examples of the olefins are ethylene and propylene. Examples of the fluoroolefins are vinyl fluoride, vinylidene fluoride, trifluoroethylene, chlorotrifluoroethylene, tetrafluoroethylene, hexafluoroethylene and hexafluoroisobutene.

There is no particular limitation on the ester side chain structure of the acrylic ester or methacrylic ester. Examples of the acrylic esters or methacrylic esters are known acrylic or methacrylic ester compounds including: acrylic or methacrylic acid alkyl ester such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate or 2-hydroxypropyl acrylate or methacrylate; acrylate or methacrylate containing an ethylene glycol group, a propylene glycol group or a tetramethylene glycol group; unsaturated amide such as acrylamide, methacrylamide, N-methylol acrylamide, N-methylol methacrylamide or diacetone acrylamide; acrylonitrile; methacrylonitrile; alkoxysilane-containing vinylsylane or acrylic or methacrylic ester; t-butyl acrylate or methacrylate; 3-oxocyclohexyl acrylate or methacrylate; adamantyl acrylate or methacrylate; alkyladamantyl acrylate or methacrylate; cyclohexyl acrylate or methacrylate; tricyclodecanyl acrylate or methacrylate; acrylate or methacrylate having a ring structure such as a lactone ring or a norbornene ring; acrylic acid; and methacrylic acid. An acrylate compound obtained by bonding a cyano group to the α-position of the above acrylate compound and an analogous compound, such as maleic acid, fumaric acid or maleic anhydride, is also usable.

Examples of the fluorine-containing acrylic esters or fluorine-containing methacrylic esters are acrylic esters or methacrylic esters each having a fluorine-containing group at the acrylic α-position or ester moiety. A cyano group may be introduced into the α-position. For example, there can suitably be used, as a monomer having a fluoroalkyl group at the α-position, a monomer in which a trifluoromethyl group, a trifluoroethyl group, a nonafluoro-n-butyl group etc. is imparted to the α-position of the above non-fluorinated acrylic ester or methacrylic ester.

On the other hand, there can be used acrylic esters or methacrylic esters in which the ester moiety is a fluorinated alkyl group e.g. a perfluoroalkyl group or a fluoroalkyl group, or in which a cyclic structure and a fluorine atom coexist in the ester moiety. The cyclic structure can be, for example, a fluorine-containing benzene ring, a fluorine-containing cyclopentane ring, a fluorine-containing cyclohexane ring, a fluorine-containing cycloheptane ring or the like, which has been substituted with a fluorine atom or a trifluoromethyl group. An acrylic ester or methacrylic ester in which the ester moiety is a fluorine-containing t-butyl ester group is also usable. Typical examples of such monomer units are 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, perfluorocyclohexylmethyl methacrylate, and the like.

As the norbornene compounds and fluorine-containing norbornene compounds, there can be used, without particular limitation, norbornene monomers having a mononuclear or multinuclear structure. Among others, suitable examples of the norbornene compounds are those formed by the Diels-Alder addition reaction of an unsaturated compound such as an allyl alcohol, a fluorine-containing allyl alcohol, an acrylic acid, an α-fluoroacrylic acid, a methacrylic acid and any of the acrylic esters, methacrylic esters, fluorine-containing acrylic esters and fluorine-containing methacrylic esters described in the present specification with cyclopentadiene or cyclohexadiene.

The styrenic compounds, fluorine-containing styrenic compounds, vinyl ethers, fluorine-containing vinyl ethers, allyl ethers, vinyl esters, vinyl silanes and the like are also usable. Examples of the styrenic compounds and fluorine-containing styrenic compounds are styrene, fluorinated styrene, hydroxystyrene, hexafluoroacetone-added styrene, styrene or hydroxystyrene in which hydrogen is substituted with a trifluoromethyl group and monomers obtained by bonding a halogen, an alkyl group or a fluoroalkyl group to the α-position of the above styrene or styrenic compound. Further, there can be used various vinyl ethers, fluorine-containing vinyl ethers, allyl ethers, vinyl esters and the like. One example of the vinyl ethers is an alkyl vinyl ether that may contain a methyl group, an ethyl group or a hydroxy group such as hydroxyethyl or hydroxybutyl. All or part of hydrogen atoms of the alkyl vinyl ether may be substituted with fluorine. Other examples of the vinyl ethers are cyclohexyl vinyl ether, cyclic vinyl ether containing a hydrogen or carbonyl bond in its cyclic structure and monomers obtained by substituting all or part of hydrogen atoms of the cyclic vinyl ether with fluorine. The allyl ethers, vinyl esters and vinyl silane can be used without particular limitation as long as they are known compounds.

Among the above base resins, it is preferable to use the base resin having a repeating unit represented by the following general formula (6).

[Chem. 52]

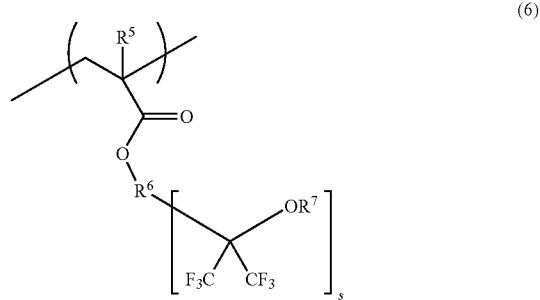

(6)

In the general formula (6), $R^5$ indicates a hydrogen atom, a halogen atom, a hydrocarbon group (e.g. $C_1$-$C_3$ alkyl group) or a fluoroalkyl group; $R^6$ indicates a linear or branched alkyl group, an alkyl group having a ring structure, an aromatic ring or a composite group thereof and may partially be fluorinated; $R^7$ indicates a hydrogen atom, a hydrocarbon group that may be branched, a fluoroalkyl group, or a cyclic group having an aromatic structure or aliphatic ring structure, and may contain an oxygen or carbonyl bond; and s indicates an integer of 1 to 2.

There is no particular limitation on $R^5$ in the general formula (6) as long as $R^5$ is either a hydrogen atom, a halogen atom, a hydrocarbon group or a fluoroalkyl group. Preferred examples of the halogen atom are fluorine, chlorine and bromine. Preferred examples of the hydrocarbon group are methyl, ethyl, propyl, isopropyl, butyl, isobutyl, sec-butyl, tert-butyl, cyclopentyl, cyclohexyl, phenyl, benzyl and phenetyl. Preferred examples of the fluoroalkyl group are those obtained by substituting all or part of hydrogen atoms of the above alkyl group with a halogen group. In particular, the hydrocarbon group and the fluoroalkyl group are preferably those having a carbon number of the order of 1 to 20, more preferably 1 to 4 in view of the ease of polymerization. More specifically, the fluoroalkyl group can suitably be trifluoromethyl (—CF₃), trifluoroethyl (—CH₂CF₃), 1,1,1,3,3,3-hexafluoroisopropyl, heptafluoroisopropyl, nonafluoro-n-butyl (—C₄F₉) or the like.

Further, $R^6$ in the general formula (6) is either a linear or branched alkyl group, an alkyl group having a cyclic structure, an aromatic ring, or a composite group thereof, that may partially be fluorinated and may have an unsaturated bond. There can be used a linear or branched alkylene group such as methylene, ethylene, isopropylene or t-butylene, a cyclic structure containing cyclobutene, cyclohexane, norbornene or adamantane, or a phenyl group, without particular limitation. Particularly preferred examples of the repeating unit structure of the general formula (6) are those represented by the following general formulas (7) to (9).

[Chem. 53]

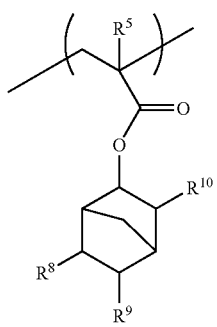

(7)

[Chem. 54]

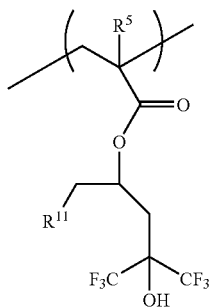

(8)

[Chem. 55]

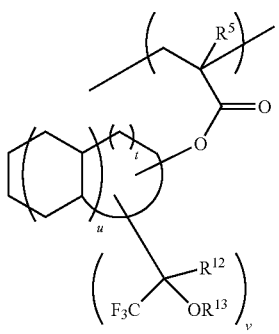

(9)

In the general formula (7), $R^5$ is the same as defined in the general formula (6); either one of $R^8$, $R^9$ and $R^{10}$ indicates a CF₃C(CF₃)(OH)CH₂— group and the other two of $R^8$, $R^9$ and $R^{10}$ indicate hydrogen atoms. In the general formula (8), $R^5$ is the same as defined in the general formula (6); and $R^{11}$ indicates a hydrogen atom, a methyl group, an ethyl group, a n-propyl group, an isopropyl group, a n-butyl group, a sec-butyl group, a tert-butyl group, a fluoromethyl group, a difluoromethyl group, a trifluoromethyl group or a perfluoroethyl group. In the general formula (9), $R^5$ is the same as defined in the general formula (6); $R^{12}$ indicates a methyl group or a trifluoromethyl group; $R^{13}$ indicates a hydrogen atom, a $C_1$-$C_{25}$ linear or $C_3$-$C_{25}$ branched or cyclic hydrocarbon group, or a $C_6$-$C_{26}$ aromatic hydrocarbon group; a part of $R^{13}$ may contain a fluorine atom, an oxygen atom or a carbonyl bond; u indicates an arbitrary integer of 0 to 2; t and v each independently indicate an arbitrary integer of 1 to 8 and satisfy a relationship of $v \leq t+2$; and, when there are a plurality of $R^{12}$ and $R^{13}$, they may be the same or different.

Specific examples of the $C_1$-$C_{25}$ linear or $C_3$-$C_{25}$ branched or cyclic hydrocarbon group and the $C_6$-$C_{26}$ aromatic hydrocarbon group usable as $R^{13}$ in the general formula (9) are methyl, ethyl, propyl, isopropyl, cyclopropyl, n-propyl, sec-butyl, tert-butyl, n-pentyl, cyclopentyl, sec-pentyl, neopentyl, hexyl, cyclohexyl, ethylhexyl, norbornel, adamantyl, vinyl, aryl, butenyl, pentenyl, ethynyl, phenyl, benzyl and 4-methoxybenzyl, each of which may be partially or fully substituted with fluorine. There can also be used oxygen-containing hydrocarbon groups such as an alkoxycarbonyl group, an acetal group and an acyl group. Examples of the alkoxycarbonyl group are tert-butoxycarbonyl, tert-amyloxycarbonyl, methoxycarbonyl, ethoxycarbonyl and i-propoxycarbonyl. Examples of the acetal group are: linear ethers such as methoxymethyl, methoxyethoxymethyl, ethoxyethyl, butoxyethyl, cyclohexyloxyethyl, benzyloxyethyl, phenethyloxyethyl, ethoxypropyl, benzyloxypropyl, phenethyloxypropyl, ethoxybutyl and ethoxyisobutyl; and cyclic ethers such as tetrahydrofuranyl and tetrahydropyranyl. Examples of the acyl group are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. All or part of hydrogen atoms of the above substituent groups can be substituted with fluorine.

In addition to the base resin having the repeating unit of the general formula (6), there can suitably be used the base resin having a repeating unit of the following general formula (10).

[Chem. 56]

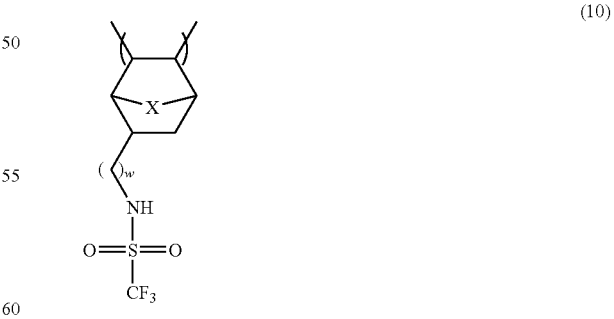

(10)

In the general formula (10), X indicates either —CH₂—, —O— or —S—; and w indicates an integer of 2 to 6.

There can also suitably be used the base resin having a repeating unit of the following general formula (11) in addition to the base resin having the repeating unit of the general formula (6) or (10).

[Chem. 57]

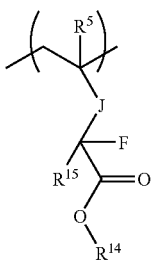

(11)

In the general formula (11), $R^5$ is the same as defined in the general formula (6); $R^{15}$ indicates a fluorine atom or a fluoroalkyl group; J indicates a divalent linking group; and $R^{14}$ indicates an acid-labile protecting group represented by either one of the following general formulas (d) to (h).

[Chem. 58]

$$R^{16}-O-C(=O)- \quad (d)$$

In the general formula (d), $R^{16}$ indicates a $C_1$-$C_4$ alkyl group that may have a substituent, a $C_3$-$C_{30}$ alicyclic hydrocarbon group that may have a substituent, or a $C_6$-$C_{14}$ aryl group that may have a substituent.

[Chem. 59]

$$R^{16}-O-CHR^{17}- \quad (e)$$

In the general formula (e), $R^{16}$ is the same as defined in the general formula (d); $R^{17}$ indicates a hydrogen atom, a $C_1$-$C_4$ alkyl group that may have a substituent, a $C_3$-$C_{30}$ alicyclic hydrocarbon group that may have a substituent, a $C_1$-$C_6$ alkoxy group that may have a substituent, a $C_2$-$C_4$ alkenyl group that may have a substituent, a $C_6$-$C_{14}$ aryl group that may have a substituent, or a $C_7$-$C_{20}$ aralkyl group that may have a substituent.

[Chem. 60]

$$CR^{18}R^{19}R^{20}- \quad (f)$$

In the general formula (f), $R^{18}$, $R^{19}$ and $R^{20}$ may be the same or different and each independently indicate a $C_1$-$C_4$ alkyl group that may have a substituent, a $C_3$-$C_{30}$ alicyclic hydrocarbon group that may have a substituent, a $C_2$-$C_4$ alkenyl group that may have a substituent, a $C_6$-$C_{14}$ aryl group that may have a substituent, or a $C_7$-$C_{20}$ aralkyl group that may have a substituent. Two of $R^{18}$, $R^{19}$ and $R^{20}$ may be bonded to each other to form a ring structure.

[Chem. 61]

$$SiR^{18}R^{19}R^{20}- \quad (g)$$

In the general formula (g), $R^{18}$, $R^{19}$ and $R^{20}$ are the same as defined in the general formula (f).

[Chem. 62]

$$R^{16}-C(=O)- \quad (h)$$

In the general formula (h), $R^{16}$ is the same as defined in the general formula (d).

In the above formulas (d) to (h), $R^{16}$, $R^{17}$, $R^{18}$, $R^{19}$ and $R^{20}$ each independently indicate a monovalent organic group as explained below. Among others, the protecting groups of the general formulas (d), (e) and (f) function as chemically amplified type and are thus particularly preferably usable in the resist composition for pattern formation by exposure to high-energy radiation.

$R^{16}$ indicates an alkyl group, an alicyclic hydrocarbon group or an aryl group. $R^{17}$ indicates a hydrogen atom, an alkyl group, an alicyclic hydrocarbon group, an alkenyl group, an aralkyl group, an alkoxy group or an aryl group. $R^{18}$, $R^{19}$ and $R^{20}$ may be the same or different and each independently indicate an alkyl group, an alicyclic hydrocarbon group, an alkenyl group, an aralkyl group or an aryl group. Two of $R^{18}$, $R^{19}$ and $R^{20}$ may be bonded to each other to form a ring structure.

The alkyl group is preferably the one having a carbon number of 1 to 4, such as methyl, ethyl, propyl, isopropyl, n-butyl, sec-butyl or tert-butyl. The alicyclic hydrocarbon group is preferably the one having a carbon number of 3 to 30, such as cyclopropyl, cyclopentyl, cyclohexyl, adamantyl, norbornyl, boronyl, tricyclodecanyl, dicyclopentenyl, norbornaneepoxy, menthyl, isomenthyl, neomenthyl, tetracyclodecanyl or steroid residue. The alkenyl group is preferably the one having a carbon number of 2 to 4, such as vinyl, propenyl, allyl or butenyl. The aryl group is preferably the one having a carbon number of 6 to 14, such as phenyl, xylyl, toluoyl, cumenyl, naphthyl or anthracenyl. These organic groups may have substituents. The aralkyl group is preferably the one having a carbon number of 7 to 20, such as benzyl, phenethyl or cumyl, that may have a substituent.

As the substituents on the above organic groups, there can be used a hydroxy group, a halogen atom (fluorine, chlorine, bromine, iodine), a nitro group, a cyano group, any of the above-mentioned alkyl and alicyclic hydrocarbon groups, an alkoxy group such as methoxy, ethoxy, hydroxyethoxy, propoxy, hydroxypropoxy, n-butoxy, isobutoxy, sec-butoxy or tert-butoxy, an alkoxycarbonyl group such as methoxycarbonyl or ethoxycarbonyl, an aralkyl group such as benzyl, phenethyl or cumyl, an aralkyloxy group, an acyl group such as formyl, acetyl, butyryl, benzoyl, cyanamyl or valeryl, an acyloxy group such as butyryloxy, any of the above-mentioned alkenyl groups, an alkenyloxy group such as vinyloxy, propenyloxy, allyloxy or butenyloxy, any of the above-mentioned aryl groups, an aryloxy group such as phenoxy, and an aryloxycarbonyl group such as benzoyloxy.

Lactone groups of the following formulas (11-1) and (11-2) are also usable.

[Chem. 63]

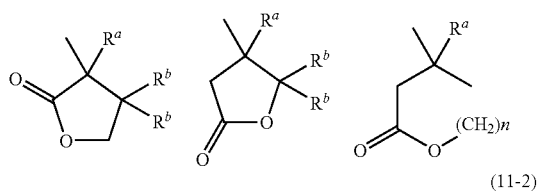

(11-1)

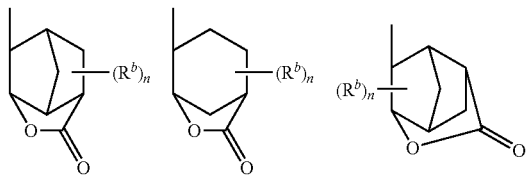

(11-2)

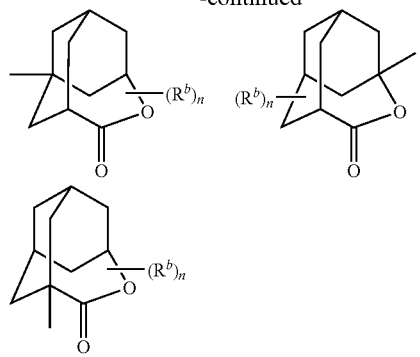

In the formulas, $R^a$ indicates a $C_1$-$C_4$ alkyl or perfluoroalkyl group; $R^b$ each independently indicates a hydrogen atom, a $C_1$-$C_4$ alkyl or perfluoroalkyl group, a hydroxy group, a carboxylic group, an alkyloxycarbonyl group, an alkoxy group or the like; and n indicates an integer of 1 to 4.

Next, the acid-labile protecting groups will be specifically indicated below.

Examples of the alkoxycarbonyl group represented by $R^{16}$—O—C(=O)— are tert-butoxycarbonyl, tert-amyloxycarbonyl, methoxycarbonyl, ethoxycarbonyl, i-propoxycarbonyl, cyclohexyloxycarbonyl, isobornyloxycarbonyl and adamantaneoxycarbonyl.

Examples of the acetal group represented by $R^{16}$—O—$CHR^{17}$— are methoxymethyl, ethoxymethyl, 1-ethoxyethyl, 1-butoxyethyl, 1-isobutoxyethyl, cyclohexyloxyethyl, benzyloxyethyl, phenethyloxyethyl, ethoxypropyl, benzyloxypropyl, phenethyloxypropyl, ethoxybutyl, 1-cyclohexyoxyethyl, ethoxyisobutyl, methoxyethoxymethyl, tetrahydropyranyl and tetrahydrofuranyl. An acetal group obtained by the addition of a vinyl ether to a hydroxy group is also usable.

Examples of the tertiary hydrocarbon group represented by $CR^{18}R^{19}R^{20}$— are tert-butyl, tert-amyl, 1,1-dimethylpropyl, 1-ethyl-1-methylpropyl, 1,1-dimethylbutyl, 1-ethyl-1-methylbutyl, 1,1-diethylpropyl, 1,1-dimethyl-1-phenylmethyl, 1-methyl-1-ethyl-1-phenylmethyl, 1,1-diethyl-1-phenylmethyl, methylcyclohexyl, ethylcyclohexyl, methylcyclopentyl, ethylcyclopentyl, isoboronyl, methyladamantyl, ethyladamantyl, isopropyladamantyl, isopropylnorbornyl and isopropyl-(4'-methylcyclohexyl).

Specific examples of the alicyclic hydrocarbon group or the alicyclic hydrocarbon-containing acid-labile protecting group are indicated as follows.

[Chem. 64]

(11-3)

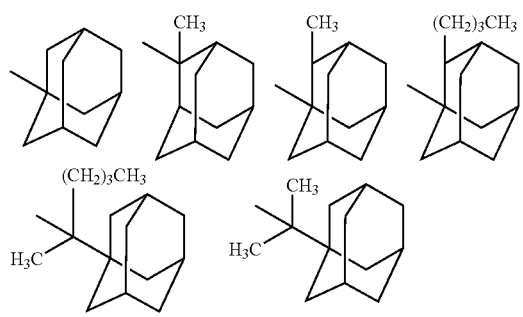

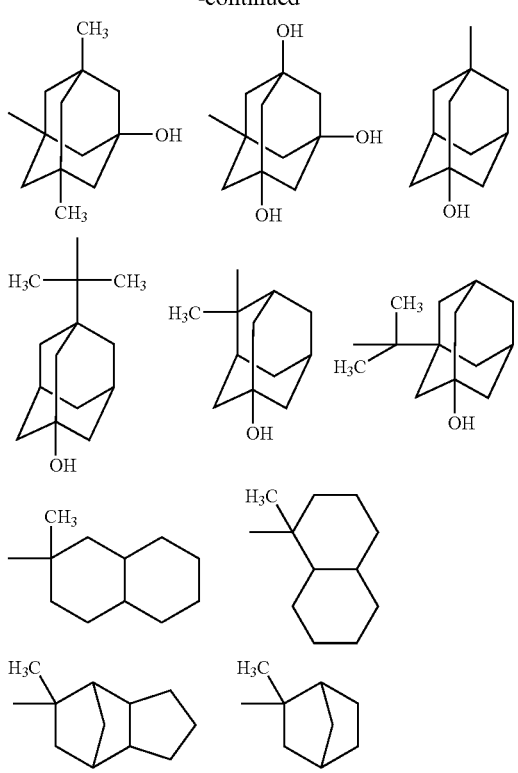

[Chem. 65]

(11-4)

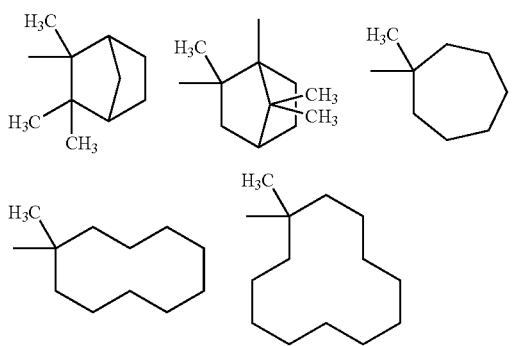

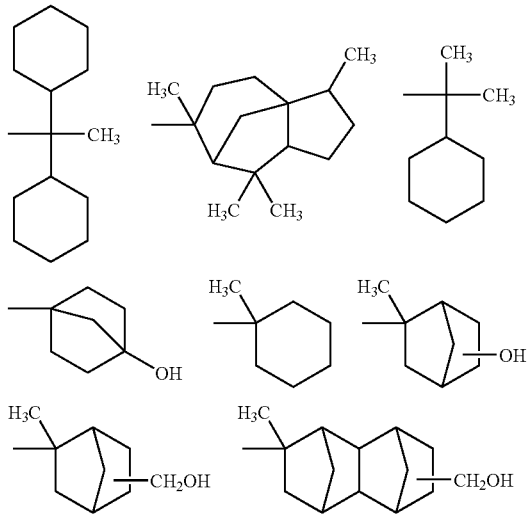

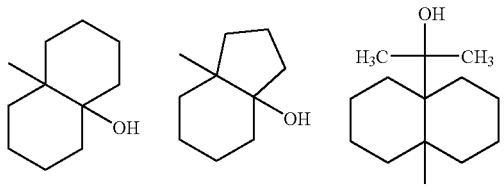

In the formulas (11-3) and (11-4), methyl (CH₃) groups may independently be replaced with ethyl groups. Further, one or two or more of the ring carbons may have a substituent as mentioned above.

Examples of the silyl group represented by $SiR^{18}R^{19}R^{20}$— are trimethylsilyl, ethyldimethylsilyl, methyldiethylsilyl, triethylsilyl, i-propyldimethylsilyl, methyl-di-i-propylsilyl, tri-i-propylsilyl, tert-butyldimethylsilyl, methyl-di-tert-butylsilyl, tri-tert-butylsilyl, phenyldimethylsilyl, methyldiphenylsilyl and triphenylsilyl.

Examples of the acyl group represented by $R^{16}$—C (=O)— are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. All or part of hydrogen atoms of these acid-labile protecting groups can be substituted with fluorine.

Specific examples of the lactone-containing acid-labile protecting group are those represented by the following formulas (11-5) to (11-10).

[Chem. 66]

(11-5)

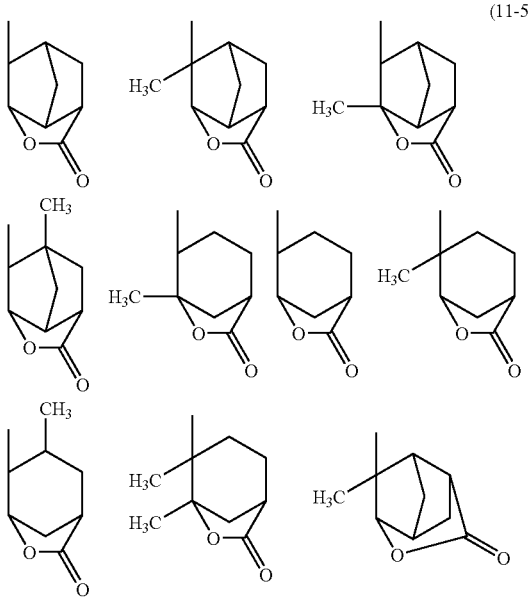

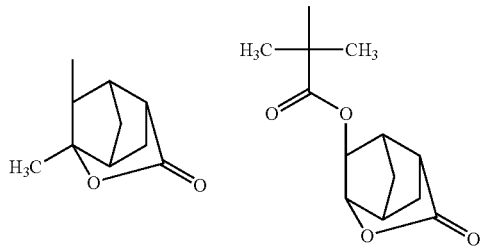

[Chem. 67]

(11-6)

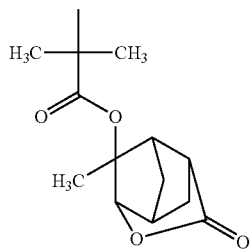

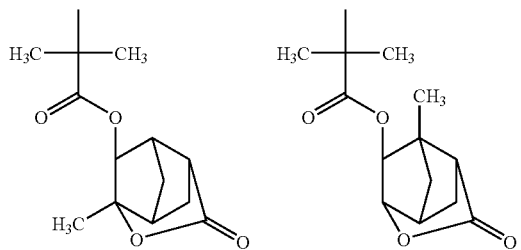

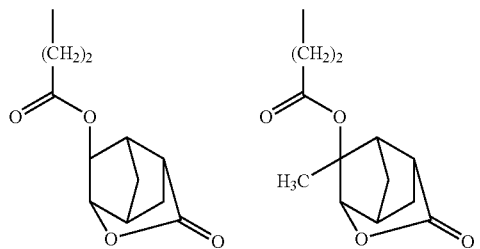

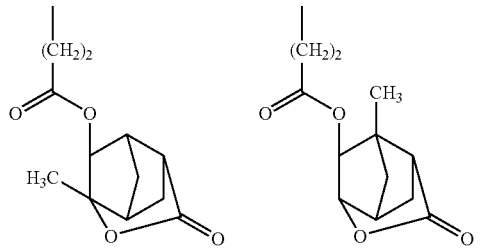

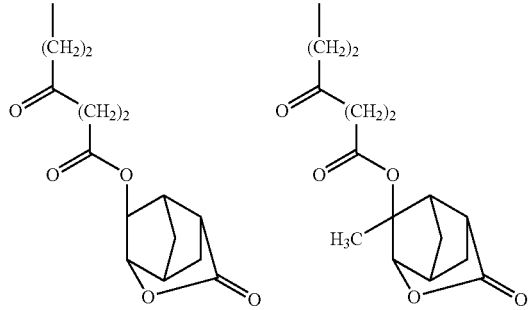

-continued
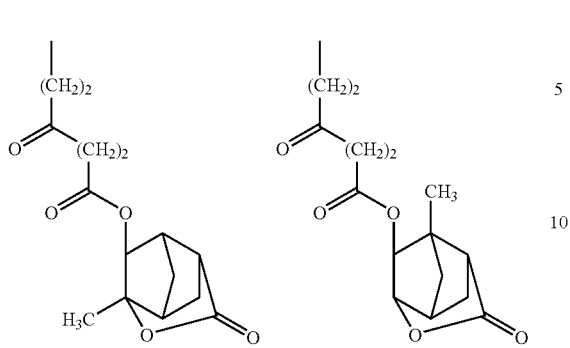
[Chem. 68]
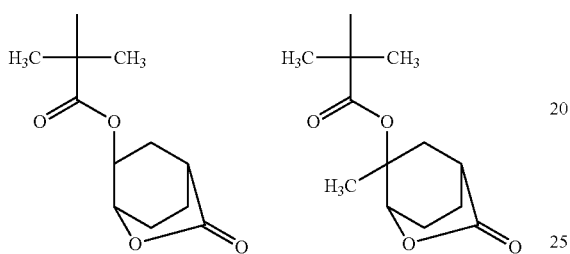
(11-7)
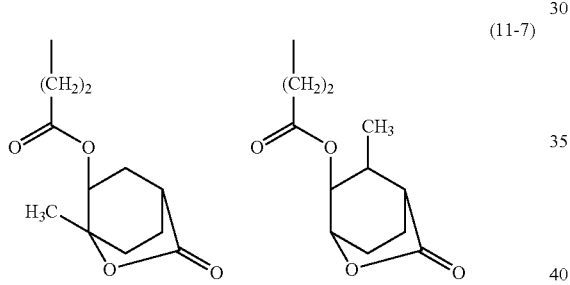
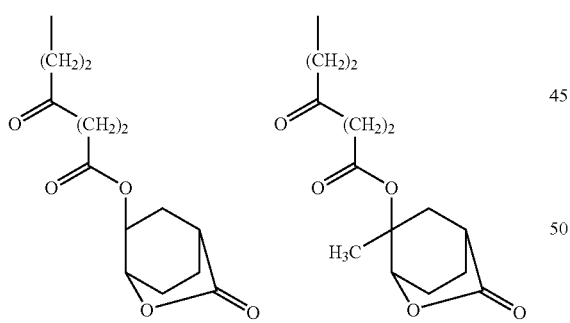
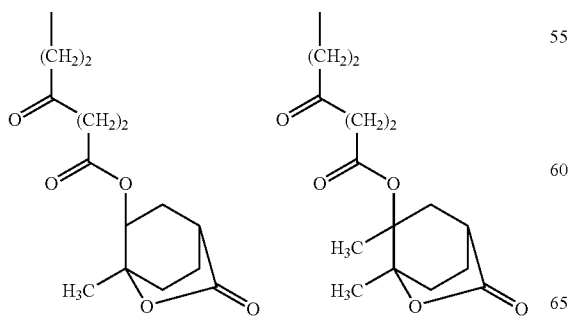
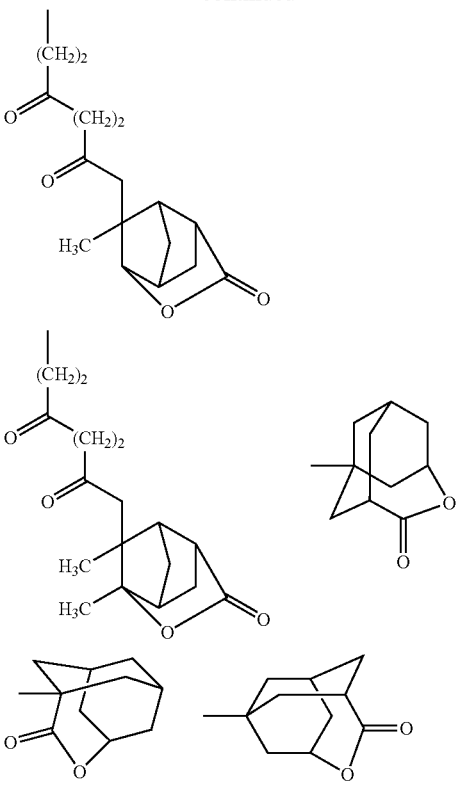
[Chem. 69]
(11-8)
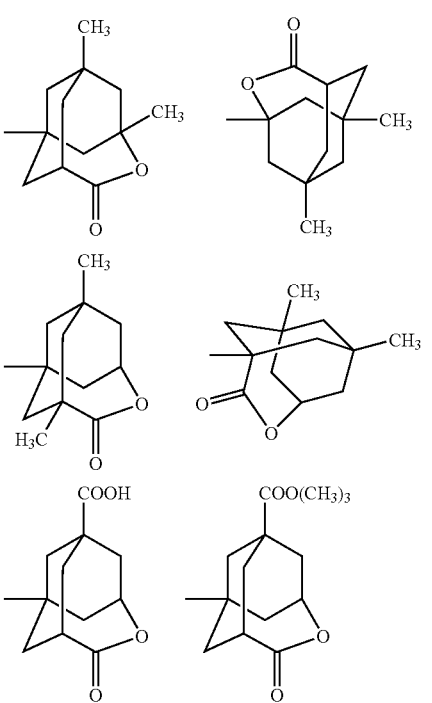

-continued

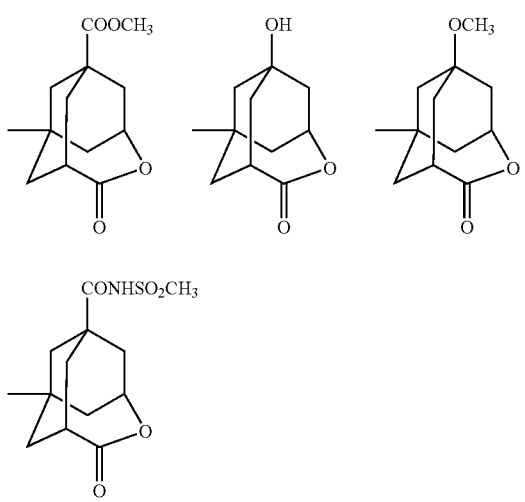

(11-9)

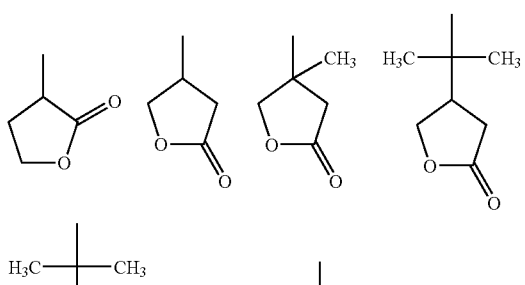

[Chem. 70]

(11-10)

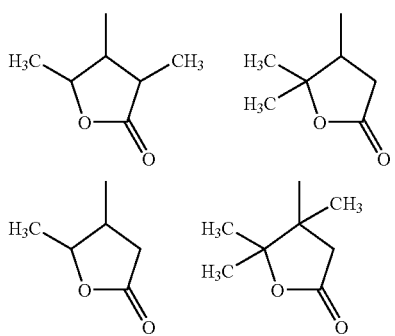

-continued

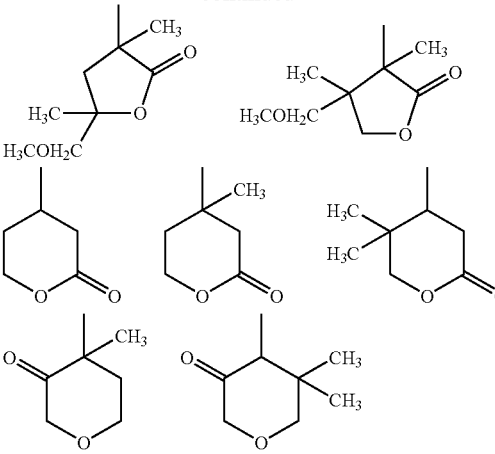

In the formulas (11-5) to (11-10), methyl ($CH_3$) groups may independently be replaced with ethyl groups.

In the case of using a ArF excimer laser as an exposure light source, the acid-labile protecting group is preferably tertiary alkyl such as tert-butyl or tert-amyl, 1-alkoxyethyl such as 1-ethoxyethyl, 1-butoxyethyl, 1-isobutoxyethyl or 1-cyclohexyethyl, alkoxymethyl such as 1-methoxymethyl or 1-ethoxymethyl, alicyclic hydrocarbon such as adamantyl or isoboronyl or alicyclic hydrocarbon-containing acid-labile protecting group, or lactone.

In the general formula (11), the linking group J is a divalent linking group formed of one, or any combination of two or more, selected from the group consisting of a single bond, $-(CR^{21}R^{22})_n-$ (where n indicates an integer of 1 to 10), $-O-$, $-C(=O)-$, $-C(=O)O-$ or $-O-C(=O)-$, thioether, ester, amide, sulfone amide, urethane and urea.

Among others, examples of the combination linking group J are $-(CR^{21}R^{22})_m-C(=O)-O-(CR^{21}R^{22})_n-$, $-(CR^{21}R^{22})_m-O-(CR^{21}R^{22})_n-$ and the like. Herein, m and n each independently indicate an integer of 0 to 10. It is preferable that: m is 0; and n is 1.

There is no particular limitation on the monovalent organic groups $R^{21}$ and $R^{22}$ in the substituted methylene group. Each of $R^{21}$ and $R^{22}$ can be a hydrogen atom, a hydroxyl group, or a $C_1$-$C_{30}$ monovalent organic group selected from the group consisting of an alkyl group, an alicyclic hydrocarbon group, a substituted alkyl group, an alkoxy group, an aryl group and a condensed-ring aromatic group. These monovalent organic groups may contain a fluorine atom, an oxygen atom, a sulfur atom, a nitrogen atom or a carbon-carbon double bond. Herein, $R^{21}$ and $R^{22}$ may be the same or different and may be bonded to each other to form a ring structure, preferably an alicyclic hydrocarbon structure.

The alkyl group is that having a carbon number of 1 to 30, preferably 1 to 12. Examples of the alkyl group are methyl, ethyl, n-propyl, isopropyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-dodecyl. Among others, particularly preferred are methyl, ethyl, n-propyl, i-propyl and the like. The substituted alkyl group is that in which one or two or more hydrogen atoms are substituted with a substituent such as $C_1$-$C_4$ alkoxy, halogen (fluorine, chlorine, bromine, iodine), acyl, acyloxy, cyano, hydroxyl, carboxy, alkoxycarbonyl or nitro, preferably fluorine. Examples of the substituted alkyl group are trifluoromethyl, pentafluoroethyl, 2,2,2-trifluoroethyl, n-heptafluoropropyl, 2,2,3,3,3-pentafluoropropyl, 3,3,3-trifluoropropyl and hexafluoroisopropyl.

Examples of the alkoxy group are those having a carbon number of 1 to 4, such as methoxy, ethoxy, propoxy and butoxy.

The aryl group is that having a carbon number of 1 to 30 and, when it is monocyclic, preferably containing 3 to 12 ring carbons, more preferably 3 to 6 ring carbons. Examples of the aryl group are phenyl, biphenyl, terphenyl, o-tolyl, m-tolyl, p-tolyl, p-hydroxyphenyl, p-methoxyphenyl, mesityl, o-cumenyl, 2,3-xylyl, 2,4-xylyl, 2,5-xylyl, 2,6-xylyl, 3,4-xylyl, 3,5-xylyl, o-fluorophenyl, m-fluorophenyl, p-fluorophenyl, o-trifluoromethylphenyl, m-trifluoromethylphenyl, p-trifluoromethylphenyl, 2,3-bistrifluoromethyl, 2,4-bistrifluoromethyl, 2,5-bistrifluoromethyl, 2,6-bistrifluoromethyl, 3,4-bistrifluoromethyl, 3,5-bistrifluoromethyl, p-chlorophenyl, p-bromophenyl and p-iodophenyl.

Examples of the $C_1$-$C_{30}$ condensed-ring aromatic group are monovalent organic groups including pentalene, indene, naphthalene, azulene, heptalene, biphenylene, indacene, acenaphthylene, fluororene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene and the like. One or two or more hydrogen atoms of the above condensed-ring aromatic group may preferably be substituted with a fluorine atom or a $C_1$-$C_4$ alkyl or fluoroalkyl substituent.

There can also be used monocyclic or polycyclic heterocyclic groups having 3 to 25 ring atoms, such as pyridyl, furil, thienyl, pyranyl, pyrrolyl, thianthrenyl, pyrazolyl, isothiazolyl, isoxazolyl, pyrazinyl, pyrimidinyl, pyridazinyl, tetrahydropyranyl, tetrahydrofuranyl, tetrahydrothiopyranyl, tetrahydrothiofuranyl and 3-tetrahydrothiophene-1,1-dioxide. One or two or more hydrogen atoms on the ring atoms of the above heterocyclic group may be substituted with an alkyl, alicyclic hydrocarbon, aryl or heterocyclic substituent. Among others, preferred are those having a monocyclic or polycyclic ether ring or lactone ring.

The alicyclic hydrocarbon group as $R^{21}$, $R^{22}$ of the linking group J or the alicyclic hydrocarbon group formed by $R^{21}$ and $R^{22}$ together with the carbon atoms bonded thereto may be monocyclic or polycyclic. Examples of such an alicyclic hydrocarbon group are those having a carbon number of 3 or more and having a monocyclo, bicyclo, tricycle or tetracyclo structure. The carbon number of the alicyclic hydrocarbon group is preferably 3 to 30, more preferably 3 to 25. The alicyclic hydrocarbon group may have a substituent.

The monocyclic alicyclic hydrocarbon group is preferably that containing 3 to 12 ring carbons, more preferably 3 to 7 ring carbons. Examples of such a monocyclic alicyclic hydrocarbon group are cyclopropyl, cyclobutyl, cyclopentyl, cyclohexyl, cycloheptyl, cyclooctyl, cyclodecanyl, cyclododecanyl, tricyclodecanyl and 4-tert-butylcyclohexyl. The polycyclic alicyclic hydrocarbon group is preferably that containing 7 to 15 ring carbons. Examples of such a polycyclic alicyclic group are adamantyl, noradamantyl, decalin residue, tricyclodecanyl, tetracyclododecanyl, norbornyl and cedrol. The alicyclic hydrocarbon group can be a spiro ring, preferably having a carbon number of 3 to 6. Preferred examples of the spiro ring are adamantyl, decalin residue, norbornyl, cedrol, cyclohexyl, cycloheptyl, cyclooctyl, cyclodecanyl and tricyclodecanyl. One or two or more hydrogen atoms on the ring atoms of the above organic group, or one or two or more hydrogen atoms on the above linking group, may be each independently substituted with a substituent such as $C_1$-$C_{25}$ alkyl or substituted alkyl, hydroxyl, alkoxy, carboxyl or alkoxycarbonyl. One or two or more hydrogen atoms of this substituent may further be substituted with fluorine or trifluoromethyl.

Herein, the alkyl group is preferably a methyl group, an ethyl group, a propyl group, an isopropyl group, a butyl group or the like (referred to as a "lower alkyl group" throughout the present specification). More preferably, the alkyl group is the one selected from the group consisting of methyl, ethyl, propyl and isopropyl. As the substituent of the substituted alkyl group, there can be used a hydroxyl group, a halogen atom, an alkoxy group and the like. The alkoxy group is, for example, that having a carbon number of 1 to 4, such as methoxy, ethoxy, propoxy, butoxy or the like. Further, the alkoxy carbonyl group is, for example, methoxycarbonyl, ethoxycarbonyl, isopropoxycarbonyl or the like.

More specifically, preferred examples of the linking group J are —O—, —C(=O)—O—, —CH$_2$—O—, —O—CH$_2$—, —CH$_2$—C(=O)—O—, —C(=O)—O—CH$_2$—, —CH$_2$—O—CH$_2$—, —CH$_2$—C(=O)—O—CH$_2$—, —C(=O)—O—CR$^{21}$R$^{22}$— where R$^{21}$ and R$^{22}$ are each independently either the hydrogen atom, the fluorine atom, the alkyl group, the substituted alkyl group or the alicyclic hydrocarbon group. Among others, particularly preferred are —C(=O)—O—CR$^{21}$—R$^{22}$— where R$^{21}$ and R$^{22}$ are each independently either the hydrogen atom or the lower alkyl group.

Further, $R^{15}$ is a fluorine atom or a fluoroalkyl group. The fluoroalkyl group is no particularly limited and is preferably that having a carbon number of 1 to 12, more preferably 1 to 3. Examples of the fluoroalkyl group are trifluoromethyl, pentafluoroethyl, 2,2,2-trifluoroethyl, n-heptafluoropropyl, 2,2,3,3,3-hentafluoropropyl, 3,3,3-trifluoropropyl and hexafluoroisopropyl. Particularly preferably as $R^3$ is fluorine or trifluoromethyl.

The base resin is preferably a polymer compound having the above repeating unit as well as having a weight-average molecular weight of 1000 to 1000000. When the molecular weight of the base resin is smaller than the above-specified range, the base resin may not have a sufficient mechanical strength and film-forming property. When the molecular weight of the base resin is greater than the above-specified range, the base resin is not preferred in view of the solvent solubility and moldability. Two or more of the above polymers may be blended together for use as the base resin.

In the case of preparing the chemically amplified positive type resist material, it is essential to use the base resin originally insoluble or difficult to dissolve in a developer and made soluble in the developer by the action of an acid. For this reason, the base resin used contains an acid labile group that can be cleaved by an acid.

The base resin in which the repeating unit contains such an acid labile group is obtained by blending and copolymerizing a polymerizable monomer having the acid labile group with a polymerizable monomer having the above repeating unit or by converting a part of a base resin having the above repeating unit to the acid labile group. There is no particular limitation on the acid labile group as long as the acid labile group can be eliminated from the resin by the action of the above-mentioned photoacid generator. The acid labile group can be an alkoxycarbonyl group, an acetal group, a silyl group, an acyl group or the like. Examples of the alkoxycarbonyl group are tert-butoxycarbonyl, tert-amyloxycarbonyl, methoxycarbonyl, ethoxycarbonyl and i-propoxycarbonyl. Examples of the acetal group are methoxymethyl, ethoxyethyl, butoxyethyl, cyclohexyloxyethyl, benzyloxyethyl, phenethyloxyethyl, ethoxypropyl, benzyloxypropyl, phenethyloxypropyl, ethoxybutyl and ethoxyisobutyl. An acetal group in which a vinyl ether has been added to a hydroxyl group can also be used. Examples of the silyl group are trimethylsilyl, ethyldimethylsilyl, methyldiethylsilyl, triethylsilyl, i-propyldimethylsilyl, methyl-di-i-propylsilyl, tri-i-propylsilyl, t-butyldimethylsilyl, methyl-di-t-butylsilyl, tri-t-butylsilyl, phenyldimethylsilyl, methyldiphenylsilyl and triphenylsilyl. Examples of the acyl group are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophthaloyl, terephthaloyl, naphtoyl, toloyl, hydroatropoyl, atropoyl, cinnamoyl, furoyl, tenoyl, nicotinoyl and isonicotinoyl. All or part of hydrogen atoms of the above acid labile group may be substituted with a fluorine atom.

[Solvent]

There is no particular limitation on the organic solvent contained in the resist material of the present invention as long as the base resin, acid generator and any other additive can be dissolved in the organic solvent. Examples of the organic solvent are: ketones such as acetone, methyl ethyl ketone, cyclohexanone, methyl isoamyl ketone and 2-heptanone; polyhydric alcohols and derivatives thereof, such as monomethyl ether, monoethyl ether, monopropyl ether, monobutyl ether or monophenyl ether of ethylene glycol, ethylene glycol monoacetate, diethylene glycol, diethylene glycol monoacetate, propylene glycol, propylene glycol monoacetate, dipropylene glycol or dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improved ease of application. These solvents can be used solely or in combination of two or more thereof.

The amount of the organic solvent used is preferably 200 to 1000 parts by weight, particularly preferably 400 to 800 parts by weight, per 100 parts by weight of the base resin.

[Pattern Formation Method]

The resist material of the present invention is suitably used for pattern formation through the steps of applying the resist material to a substrate; after heat treating the applied resist material, exposing the applied resist material to a high-energy radiation of 300 nm or less wavelength through a photomask; and, after heat treating the exposed resist material as needed, developing the exposed resist material with a developer.

Any conventional photoresist pattern formation process can be adopted for the use of the resist material of the present invention. Namely, the resist material is first applied to a substrate e.g. silicon wafer with a spinner etc. and dried to form a photosensitive layer. The photosensitive layer is exposed to a high-energy ray by an exposure device through a desired mask pattern, and then, subjected to heat treatment. Subsequently, the photosensitive layer is developed with a developer e.g. 0.1 to 10 wt % aqueous tetramethylammonium hydroxide solution or aqueous alkaline solution. By this pattern formation method, it is possible to obtain a resist pattern faithful to the mask pattern. Various miscible additives, such as additional resin, quencher, plasticizer, stabilizer, coloring agent, surfactant, viscosity improver, leveling agent, antifoaming agent, compatibilizer, primer and antioxidant, may be added to the resist material as desired.

There is no particular limitation on the high-energy radiation of 300 nm or less wavelength in the present invention. Examples of the high-energy radiation are ultraviolet ray, far-ultraviolet ray, extreme-ultraviolet ray, electron beam, X-ray, excimer laser, γ-ray and synchrotron radiation. For fine processing, it is effective to use an exposure device having a source for generating a short-wavelength, high-energy ray such as an ArF excimer laser, a KrF excimer laser or an EUV. It is further effective to use a liquid immersion exposure device that enables more efficient fine processing in numerical aperture and effective wavelength by the application of a medium with less absorption of the high-energy ray, such as water or fluorinated solvent, to a part of the optical path. The present resist material is suitable for use in this device.

Among others, a particularly preferred example of the pattern formation method is immersion lithography process using an ArF excimer laser of 193 nm wavelength as the high-energy radiation and alloying insertion of water, or a liquid of higher refractive index than that of the air, between the substrate and projector lens.

EXAMPLES

The present invention will be described in more detail below by way of the following working examples, reference examples and comparative examples. It should be noted that the following working examples are not intended to limit the present invention thereto.

Preparation of Sulfonic Acid Salts and Sulfonic Acid Onium Salts

Example 1-1

Preparation of 2-bromo-2,2-difluoroethyl-cyclohexylcarbamate

[Chem. 71]

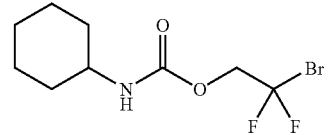

A 50-mL reaction vessel was charged with 10.0 g (79.9 mmol/1.0 equivalent) of cyclohexyl isocyanate and 25.1 g (156 mmol/2.0 equivalent) of bromo difluoro ethanol. The resulting solution was stirred at 40° C. for about 18 hours and, after stopping the stirring, subjected to vacuum drying at 60° C., thereby yielding 23.1 g of 2-bromo-2,2-difluoroethyl-cyclohexylcarbamate as a target product. The yield of the product was 85%.

Properties of 2-bromo-2,2-difluoroethyl-cyclohexylcarbamate $^1$H NMR (CDCl$_3$) δ 4.77 (br, 1H, NH), 4.55 (t, J=11.7 Hz, 2H, CH$_2$—O), 3.46 (m, 1H, CH), 1.93 (m, 2H, CH$_2$), 1.70 (m, 2H, CH$_2$), 1.59 (m, 1H), 1.33 (m, 2H, CH$_2$), 1.15 (m, 3H).

$^{19}$F NMR (CDCl$_3$) δ-57.0 (t, J=12 Hz, 2F).

Example 1-2

Preparation of sodium cyclohexylcarbamic acid-2,2-difluoroethylsulfonate

[Chem. 72]

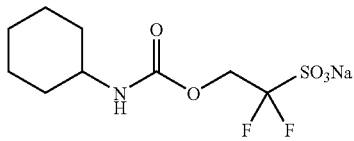

A 500-mL reaction vessel was charged with 23.0 g (67.5 mmol) of 2-bromo-2,2-difluoroethyl-cyclohexylcarbamate, followed by adding thereto 100 g of acetonitrile and dissolving the 2-bromo-2,2-difluoroethyl-cyclohexylcarbamate in the acetonitrile. The resulting solution was mixed with 29.0 g (167 mmol) of sodium dithionite, 17.0 g (202 mmol) of sodium hydrogen carbonate and 100 g of water, and then, stirred at 60° C. for about 113 hours. After stopping the stirring, the solution was separated into two phases. The aqueous phase was extracted four times with 100 g of acetonitrile. The thus-obtained organic phases were combined together. The acetonitrile solvent was removed from the combined organic phase fraction by concentration. With this, 38.3 g (purity: 42%) of a light-yellow solid substance was obtained.

A 200-mL reaction vessel was charged with 38.2 g (54.2 mmol, purity: 42%) of the obtained solid substance, followed by adding thereto 100 g of water and dissolving the solid substance in the water. This solution was mixed with 6.75 g (59.5 mmol) of 30% hydrogen peroxide and stirred at 50° C. for 5 hours. After stopping the stirring, the solvent was removed from the solution. The resulting residual substance was washed twice with diisopropyl ether and then dried, thereby yielding 32.0 g of sodium cyclohexylcarbamic acid-2,2-difluoroethylsulfonate as a product. The purity of the product was 47%; and the yield of the product was 71%.

Properties of sodium cyclohexylcarbamic acid-2,2-difluoroethylsulfonate $^1$H NMR (DMSO-$d_6$) δ 4.46 (t, J=16.1 Hz, 2H, CH$_2$), 3.23 (m, 1H, NH), 1.70 (m, 1H), 1.63 (m, 2H), 1.50 (m, 1H), 1.24-0.90 (m, 6H).
$^{19}$F NMR (DMSO-$d_6$) δ-113.7 (t, J=17 Hz, 2F).

Example 2

Preparation of triphenylsulfonium cyclohexylcarbamic acid-2,2-difluoroethylsulfonate

[Chem. 73]

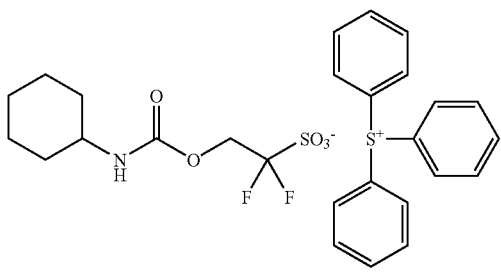

A 300-mL reaction vessel was charged with 31.85 g (purity: 47%, 48.0 mmol) of sodium cyclohexylcarbamic acid-2,2-difluoroethylsulfonate, 15.8 g (52.9 mmol) of triphenylsulfonium chloride, 170 g of water and 30 g of chloroform. The resulting solution was stirred for 4 hours at room temperature and separated into two phases. The aqueous phase was extracted with chloroform. The thus-obtained organic phases were combined together. The combined organic phase faction was washed six times with water, subjected to concentration, washed three times with diisopropyl ether, and then, dried, thereby yielding 24.5 g of triphenylsulfonium cyclohexylcarbamic acid-2,2-difluoroethylsulfonate as a target product. The purity of the product was 76%; and the yield of the product was 70%.

Properties of triphenylsulfonium cyclohexylcarbamic acid-2,2-difluoroethylsulfonate $^1$H NMR (CDCl$_3$) δ 7.80-7.58 (m, 15H), 4.83 (m, 1H, NH), 4.68 (t, J=15.1 Hz, 2H, CH$_2$), 3.38 (m, 1H), 1.83 (m, 2H), 1.61 (m, 2H), 1.52 (m, 1H), 1.23 (m, 2H), 1.08 (m, 3H).
$^{19}$F NMR (CDCl$_3$) δ-114.36 (t, J=14.6 Hz, 2F).
$^{13}$C NMR (CDCl$_3$) δ 154.4 (C=O), 134.4, 131.4, 131.0, 124.2, 119.2 (t, J=278 Hz), 62.2 (t, J=21 Hz), 49.8, 32.8, 25.1, 24.5.

Example 3-1

Preparation of adamantane-1-yl-carbamic acid-2-bromo-2,2-difluoroethyl ester

[Chem. 74]

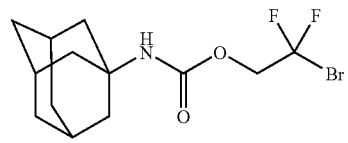

A 20-mL reaction vessel was charged with 4.86 g (purity: 97%, 26.6 mmol) of 1-adamantyl isocyanate, 10.7 g (66.5 mmol/2.5 equivalent) of bromo difluoro ethanol and 10 mL of THF (dehydrated form) under nitrogen atmosphere The resulting solution was stirred at 40° C. and cooled to room temperature. An insoluble substance was filtered out of the solution. The solution was then subjected to vacuum drying, thereby yielding 9.15 g of adamantane-1-yl-carbamic acid-2-bromo-2,2-difluoroethyl ester as a target product. The purity of the product was 74%; and the yield of the product was 73%.

Properties of adamantane-1-yl-carbamic acid-2-bromo-2,2-difluoroethyl ester $^1$H NMR (CDCl$_3$) δ 4.79 (br, 1H, NH), 4.52 (t, J=11.5 Hz, 2H, CH$_2$), 2.09 (m, 3H), 1.94 (m, 6H), 1.67 (m, 6H).
$^{19}$F NMR (CDCl$_3$) δ-56.82 (t, J=9.8 Hz, 2F).

Example 3-2

Preparation of sodium adamantane-1-yl-carbamic acid-2,2-difluoroethylsulfonate

[Chem. 75]

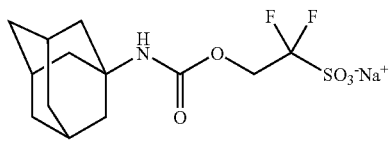

A 100-mL reaction vessel was charged with 9.0 g (purity: 73%, 19.4 mmol) of adamantane-1-yl-carbamic acid-2-bromo-2,2-difluoroethyl ester, followed by adding thereto 50 g of acetonitile and dissolving the adamantane-1-yl-carbamic acid-2-bromo-2,2-difluoroethyl ester in the acetonitrile. The resulting solution was mixed with 13.2 g (75.8 mmol) of sodium dithionite, 7.35 g (87.5 mmol) of sodium hydrogen carbonate and 50 g of water, and then, stirred at 60° C. for about 145 hours. After stopping the stirring, the solution was separated into two phases. The aqueous phase was extracted four times with 100 g of acetonitrile. The thus-obtained organic phases were combined together. The acetonitile solvent was removed from the combined organic phase fraction by concentration. With this, 31.3 g (purity: 17%) of a light-yellow solid substance was obtained.

A 200-mL reaction vessel was charged with 31.32 g (15.6 mmol, purity: 17%) of the obtained solid substance, followed by adding thereto 100 g of water and dissolving the solid substance in the water. This solution was mixed with 6.00 g (52.9 mmol) of 30% hydrogen peroxide and stirred at 50° C. for 44 hours. After stopping the stirring, the solvent was removed from the solution. The resulting residual substance was washed twice with diisopropyl ether and then dried, thereby yielding 28.01 g of sodium adamantane-1-yl-carbamic acid-2,2-difluoroethylsulfonate as a target product. The purity of the product was 15%; and the yield of the product was 61%.

Properties of sodium adamantane-1-yl-carbamic acid-2,2-difluoroethylsulfonate $^1$H NMR (DMSO-$d_6$) δ 4.40 (t, 2H, $CH_2$—O), 2.80 (br, 1H, OH), 1.97 (m, 3H), 1.83 (m, 6H), 1.56 (m, 6H).
$^{19}$F NMR (DMSO-$d_6$) δ-113.56 (t, J=14.6 Hz, 2F).

Example 4

Preparation of triphenylsulfonium adamantane-1-yl-carbamic acid-2,2-difluoroethylsulfonate

[Chem. 76]

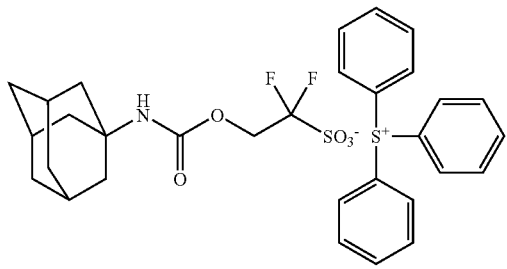

A 500-mL reaction vessel was charged with 28.0 g (purity: 15%, 11.8 mmol) of adamantane-1-yl-carbamic acid-2-bromo-2,2-difluoroethyl sulfonic acid, 4.4 g (14.5 mmol) of triphenylsulfonium chloride, 100 g of water and 50 g of chloroform. The resulting solution was stirred for 4 hours at room temperature and separated into two phase.

The aqueous phase was extracted with chloroform. The obtained chloroform phases were combined together. The combined chloroform phase fraction was washed four times with water, subjected to concentration, washed with diisopropyl ether, and then, dried, thereby yielding 6.50 g of triphenylsulfonium adamantane-1-yl-carbamic acid-2,2-difluoroethylsulfonate as a target product. The purity of the product was 78%; and the yield of the product was 92%.

Properties of triphenylsulfonium adamantane-1-yl-carbamic acid-2,2-difluoroethylsulfonate $^1$H NMR (CDCl$_3$) δ 7.90-7.58 (m, 15H), 4.72 (br, NH), 4.64 (t, J=14.9 Hz, 2H, $CH_2$), 1.99 (m, 3H), 1.83 (m, 6H), 1.58 (m, 6H).
$^{19}$F NMR (CDCl$_3$) δ-114.27.
$^{13}$C NMR (CDCl$_3$) δ 152.9 (C=O), 134.2, 131.2, 130.9, 124.2, 119.1 (t, J=Hz), 61.6, 50.4, 41.3, 35.9, 29.0.

Performance Evaluation of Photoacid Generators

The above-prepared sulfonic acid onium salts (triphenylsulfonium cyclohexylcarbamic acid-2,2-difluoroethylsulfonate (PAG 1) and triphenylsulfonium adamantane-1-yl-carbamic acid-2,2-difluoroethylsulfonate (PAG 2)) were evaluated as follows. For comparison purposes, triphenylsulfonium cyclohexyloxycarbonyldifluoromethanesulfonate (PAG 3), triphenylsulfonium (adamantane-1-yl-methyl)oxycarbonyldifluoromethanesulfonate (PAG 4), triphenylsulfonium 2-cyclohexylcarbonyloxy-1,1-difluoroethanesulfonate (PAG 5), triphenylsulfonium 2-(1'-adamantane)carbonyloxy-1,1-difluoroethanesulfonate (PAG 6) and triphenylsulfonium nonafluorobuthanesulfonate (PAG 7) were also evaluated.

[Chem. 77]

(PAG1)

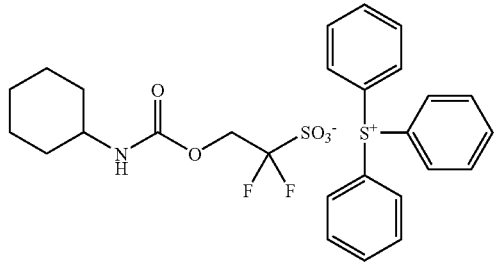

(PAG2)

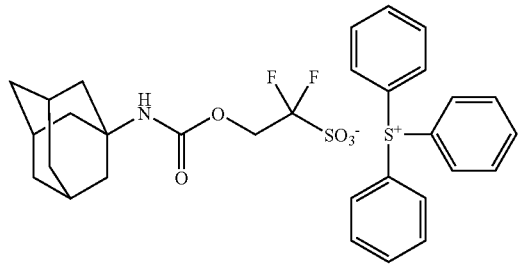

(PAG3)
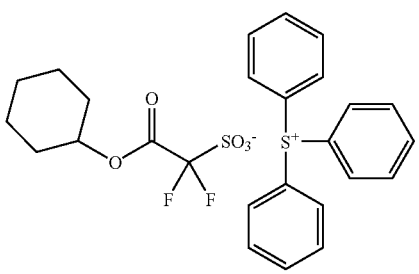

(PAG4)
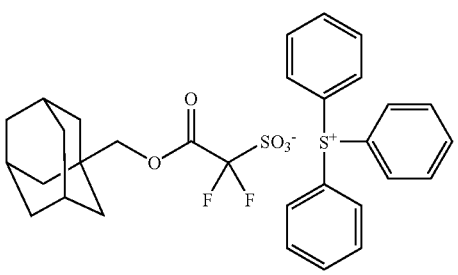

(PAG5)
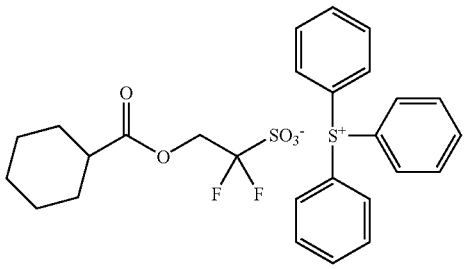

(PAG6)
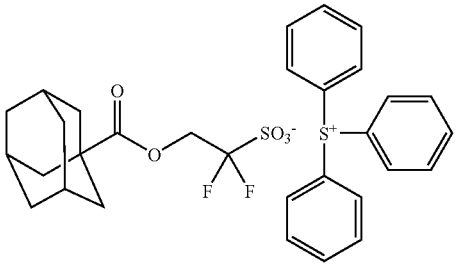

(PAG7)
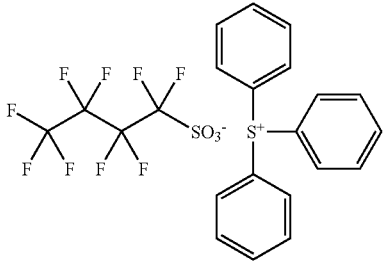

1) Resist Solvent Solubility

Using propylene glycol monomethyl ether acetate (PGMEA) as a resist solvent, the solubility of PAG 1 to PAG 6 in the resist solvent was measured. The solubility measurement results (the parts by weight of PAG dissolved in 100 parts by weigh of PGMEA) are indicated in TABLE 1.

TABLE 1

| Example No. | PAG | Solubility |
| --- | --- | --- |
| Example 5 | PAG 1 | 0.9 |
| Comparative Example 1 | PAG 3 | 0.4 |
| Reference Example 1 | PAG 5 | 0.3 |
| Example 6 | PAG 2 | 0.7 |
| Comparative Example 2 | PAG 4 | 0.3 |
| Reference Example 2 | PAG 6 | 0.2 |

As indicated above, the resist solvent solubility of the urethane bond-containing sulfonic acid onium salts of the present invention (PAG 1 and PAG 2 of Examples 5 and 6) was twice or more higher than that of the urethane bond-free sulfonic acid onium salts (PAG 3 to PAG 6 of Comparative Examples 1 and 2 and Reference Examples 1 and 2).

2) Resist Compatibility and Resist Resolution

Resist compositions were prepared using the above sulfonic acid onium salts PAG 1 and PAG 2 as acid generators and the following polymers (Resin 1 to 5) as base resins. Resist solutions were obtained by filtering the resist compositions with 0.2-1.1m membrane filters, respectively.

[Chem. 78]

(Resin 1)
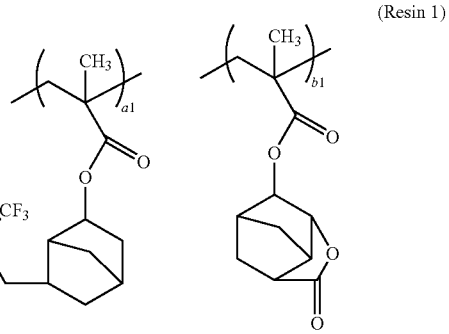

(a1 = 0.20, b1 = 0.45, c1 = 0.35, MW = 8,200)

(Resin 2)
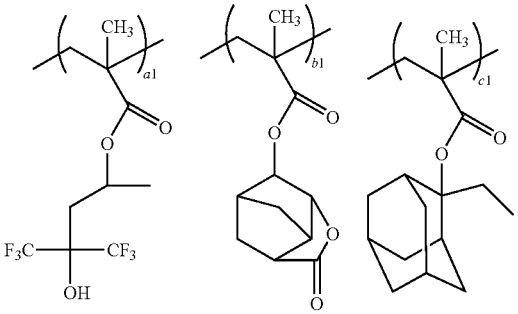

(a1 = 0.25, b1 = 0.45, c1 = 0.30, MW = 9,000)

(Resin 3)

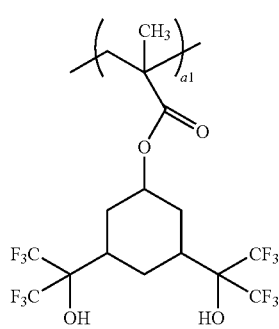

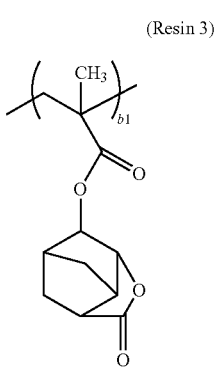

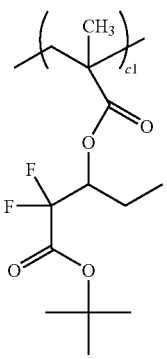

(a1 = 0.20, b1 = 0.45, c1 = 0.35, MW = 8,600)

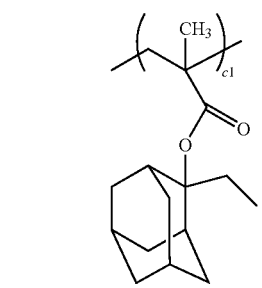

(a1 = 0.20, b1 = 0.45, c1 = 0.35, MW = 8,400)

(Resin 4)

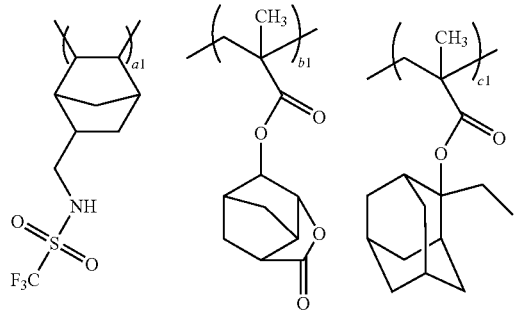

(a1 = 0.10, b1 = 0.45, c1 = 0.45, MW = 7,700)

(Resin 5)

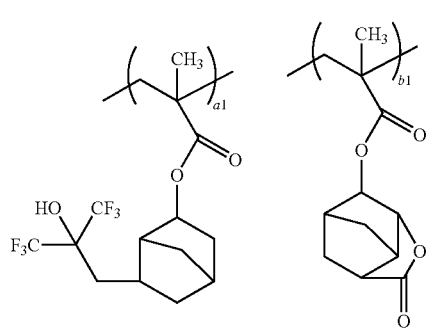

Each of the obtained resist solutions was spin-coated on a silicon wafer to form a resist film of 250 nm thickness. The resist film was prebaked at 110° C., exposed to a 248-nm ultraviolet ray through a photomask, and then, subjected to post exposure baking treatment at 120° C. After that, the resist film was developed with a 38 wt % aqueous tetramethylammonium hydroxide solution for 1 minute at 23° C. The resist compositions and evaluation results are indicated in TABLE 2.

TABLE 2

| Example | Resin (pts. wt.) | Acid generator (pts. wt.) | Solvent (pts. wt.) | Compatibility | Pattern shape |
|---|---|---|---|---|---|
| 7 | Resin 1 (40) | PAG 1 (1.0) | PGMEA (400) | Good | Clean rectangular shape |
| 8 | Resin 1 (40) | PAG 2 (1.0) | PGMEA (400) | Good | Clean rectangular shape |
| 9 | Resin 2 (40) | PAG 1 (1.0) | PGMEA (400) | Good | Clean rectangular shape |
| 10 | Resin 2 (40) | PAG 2 (1.0) | PGMEA (400) | Good | Clean rectangular shape |
| 11 | Resin 3 (40) | PAG 1 (1.0) | PGMEA (400) | Good | Clean rectangular shape |
| 12 | Resin 3 (40) | PAG 2 (1.0) | PGMEA (400) | Good | Clean rectangular shape |
| 13 | Resin 4 (40) | PAG 1 (1.0) | PGMEA (400) | Good | Clean rectangular shape |
| 14 | Resin 4 (40) | PAG 2 (1.0) | PGMEA (400) | Good | Clean rectangular shape |
| 15 | Resin 5 (40) | PAG 1 (1.0) | PGMEA (400) | Good | Clean rectangular shape |
| 16 | Resin 5 (40) | PAG 2 (1.0) | PGMEA (400) | Good | Clean rectangular shape |

For comparison purposes, the above sulfonic acid onium salts PAG 3, PAG 4 and PAG 7 were tested for the resist compatibility and resist resolution under the same conditions as to the above working examples. The resist compositions and evaluation results are indicated in TABLE 3.

TABLE 3

| Comparative Example | Resin (pts. wt.) | Acid generator (pts. wt.) | Solvent (pts. wt.) | Compatibility | Pattern shape |
|---|---|---|---|---|---|
| 3 | Resin 1 (40) | PAG 3 (1.0) | PGMEA (400) | Slightly poor | Slightly distorted rectangular shape |
| 4 | Resin 1 (40) | PAG 4 (1.0) | PGMEA (400) | Good | Slightly distorted rectangular shape |
| 5 | Resin 1 (40) | PAG 7 (1.0) | PGMEA (400) | Good | Slightly head-swollen shape |
| 6 | Resin 2 (40) | PAG 3 (1.0) | PGMEA (400) | Slightly poor | Slightly distorted rectangular shape |
| 7 | Resin 2 (40) | PAG 4 (1.0) | PGMEA (400) | Good | Clean rectangular shape |
| 8 | Resin 2 (40) | PAG 7 (1.0) | PGMEA (400) | Slightly poor | Slightly head-swollen shape |
| 9 | Resin 3 (40) | PAG 3 (1.0) | PGMEA (400) | Slightly poor | Slightly distorted rectangular shape |
| 10 | Resin 3 (40) | PAG 4 (1.0) | PGMEA (400) | Good | Clean rectangular shape |
| 11 | Resin 3 (40) | PAG 7 (1.0) | PGMEA (400) | Slightly poor | Slightly head-swollen shape |
| 12 | Resin 4 (40) | PAG 3 (1.0) | PGMEA (400) | Slightly poor | Slightly distorted rectangular shape |
| 13 | Resin 4 (40) | PAG 4 (1.0) | PGMEA (400) | Good | Slightly distorted rectangular shape |
| 14 | Resin 4 (40) | PAG 7 (1.0) | PGMEA (400) | Slightly poor | Slightly head-swollen shape |
| 15 | Resin 5 (40) | PAG 3 (1.0) | PGMEA (400) | Slightly poor | Slightly distorted rectangular shape |
| 16 | Resin 5 (40) | PAG 4 (1.0) | PGMEA (400) | Good | Slightly distorted rectangular shape |
| 17 | Resin 5 (40) | PAG 7 (1.0) | PGMEA (400) | Slightly poor | Slightly distorted rectangular shape |

As seen from the results of TABLES 2 and 3, the sulfonic acid onium salts of the present invention (PAG 1 and PAG2) had higher resist compatibility than that of the conventional salts; and the resist materials using the sulfonic acid onium salts of the present invention (PAG 1 and PAG2) achieved high pattern resolution.

The invention claimed is:

1. A fluorinated sulfonic acid salt or fluorinated sulfonic acid group-containing compound having a structure represented by the following general formula (A)

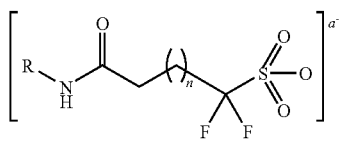
(A)

where n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; and a indicates 1 or 0.

2. A fluorinated sulfonic acid onium salt represented by the following general formula (3)

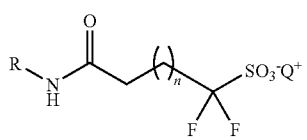
(3)

where n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; and $Q^+$ indicates a sulfonium cation of the following general formula (a) or the following general formula (b) or a iodonium cation of the following general formula (c)

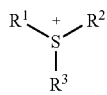
(a)

where $R^1$, $R^2$ and $R^3$ each independently indicate a substituted or unsubstituted $C_1$-$C_{10}$ linear or branched alkyl, alkenyl or oxoalkyl group, or a substituted or unsubstituted $C_6$-$C_{18}$ aryl, aralkyl or aryloxoalkyl group; and two or more of $R^1$, $R^2$ and $R^3$ may be bonded to each other to form a ring structure with a sulfur atom in the formula

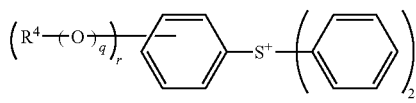

where $R^4$ indicates a substituted or unsubstituted $C_1$-$C_{20}$ linear, branched or cyclic alkyl or alkenyl group, or a substituted or unsubstituted $C_6$-$C_{14}$ aryl group; r indicates an integer of 1 to 5; and q indicates 0 or 1

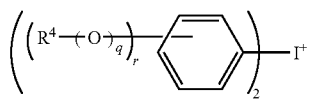

where $R^4$ indicates a substituted or unsubstituted $C_1$-$C_{20}$ linear, branched or cyclic alkyl or alkenyl group, or a substituted or unsubstituted $C_6$-$C_{14}$ aryl group; r indicates an integer of 1 to 5; and q indicates 0 or 1.

3. A fluorinated N-sulfonyloxyimide compound represented by the following general formula (4)

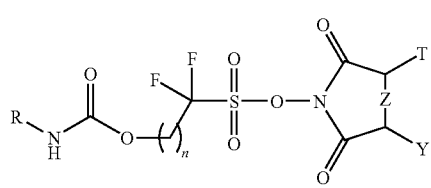

where n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; Z indicates a single bond, a double bond, a methylene group or an oxygen atom; T and Y each independently indicate a hydrogen atom or a substituted or unsubstituted $C_1$-$C_{10}$ alkyl group; and T and Y may form an aliphatic cyclic structure, an aromatic ring structure or a heterocyclic structure in cooperation with each other and with carbon atoms bonded thereto.

4. A fluorinated oxime sulfonate compound represented by the following general formula (5)

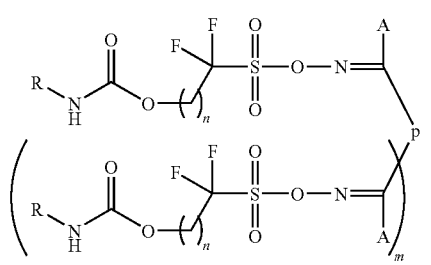

where n each independently indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; m indicates 0 or 1; p indicates a substituted or unsubstituted $C_1$-$C_{20}$ alkyl group or a substituted or unsubstituted $C_6$-$C_{15}$ aryl group in the case of m=0 and indicates a single bond, a substituted or unsubstituted $C_1$-$C_{20}$ alkylene group or a substituted or unsubstituted $C_6$-$C_{15}$ arylene group in the case of m=1; A indicates a cyano group, a trifluoromethyl group, a perfluoroethyl group, a perfluoropropyl group, a 5H-perfluoropentyl group, a 6H-perfluorohexyl group, a nitro group or a methyl group; and, in the case of m=1, both of A may be bonded to each other to form a six-carbon ring with carbon atoms bonded thereto.

5. A fluorinated sulfonic acid salt represented by the following general formula (1)

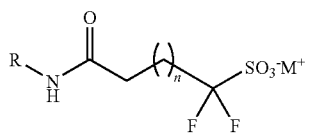

where n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; and $M^+$ indicates a lithium ion, a sodium ion, a potassium ion, an ammonium ion or a tetramethylammonium ion.

6. A photoacid generator for a chemically amplified resist material, which is sensitive to a high-energy radiation selected from ultraviolet ray, far-ultraviolet ray, extreme-ultraviolet ray, electron beam, X-ray, excimer laser, γ-ray and synchrotron radiation and is capable of generating a fluorinated sulfonic acid of the following general formula (2) by exposure to the high-energy radiation

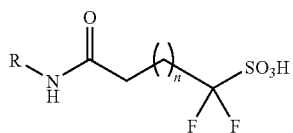

where n indicates an integer of 1 to 10; and R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group.

7. The photoacid generator according to claim 6, wherein the photoacid generator contains at least one of a fluorinated sulfonic acid onium salt represented by the following general formula (3), a fluorinated N-sulfonyloxyimide compound represented by the following general formula (4) and a fluorinated oxime sulfonate compound represented by the following general formula (5):

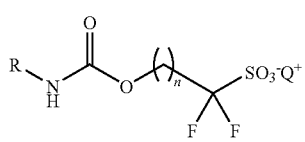

where n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; and $Q^+$ indicates a sulfonium cation of the following general formula (a) or the following general formula (b) or a iodonium cation of the following general formula (c)

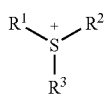
(a)

where $R^1$, $R^2$ and $R^3$ each independently indicate a substituted or unsubstituted $C_1$-$C_{10}$ linear or branched alkyl, alkenyl or oxoalkyl group, or a substituted or unsubstituted $C_6$-$C_{18}$ aryl, aralkyl or aryloxoalkyl group; and two or more of $R^1$, $R^2$ and $R^3$ may be bonded to each other to form a ring structure with a sulfur atom in the formula

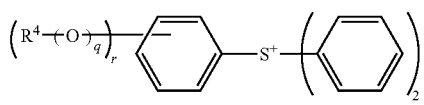
(b)

where $R^4$ indicates a substituted or unsubstituted $C_1$-$C_{20}$ linear branched or cyclic alkyl or alkenyl group, or a substituted or unsubstituted $C_6$-$C_{14}$ aryl group; r indicates an integer of 1 to 5; and q indicates 0 or 1

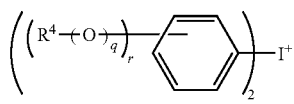
(c)

where $R^4$ indicates a substituted or unsubstituted $C_1$-$C_{20}$ linear, branched or cyclic alkyl or alkenyl group, or a substituted or unsubstituted $C_6$-$C_{14}$ aryl group; r indicates an integer of 1 to 5; and q indicates 0 or 1;

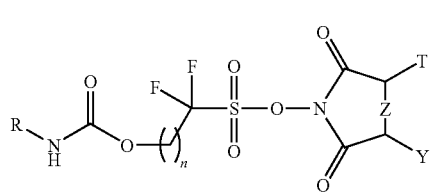
(4)

where n indicates an integer of 1 to 10; R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; Z indicates a single bond, a double bond, a methylene group or an oxygen atom; T and Y each independently indicate a hydrogen atom or a substituted or unsubstituted $C_1$-$C_{10}$ alkyl group; and T and Y may form an aliphatic cyclic structure, an aromatic ring structure or a heterocyclic structure in cooperation with each other and with carbon atoms bonded thereto; and

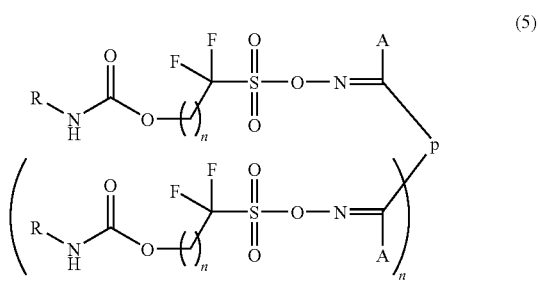
(5)

where n each independently indicates an integer of 1 to 10; R indicates a substituted or unsubstituted $C_1$-$C_{20}$ linear branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group; m indicates 0 or 1; p indicates a substituted or unsubstituted $C_1$-$C_{20}$ alkyl group or a substituted or unsubstituted $C_6$-$C_{15}$ aryl group in the case of m=0 and indicates a single bond, a substituted or unsubstituted $C_1$-$C_{20}$ alkylene group or a substituted or unsubstituted $C_6$-$C_{15}$ arylene group in the case of m=1; A indicates a cyano group, a trifluoromethyl group, a perfluoroethyl group, a perfluoropropyl group, a 5H-perfluoropentyl group, a 6H-perfluorohexyl group, a nitro group or a methyl group; and, in the case of m=1, both of A may be bonded to each other to form a six-carbon ring with carbon atoms bonded thereto.

8. A method for generating a fluorinated sulfonic acid of the following general formula (2)

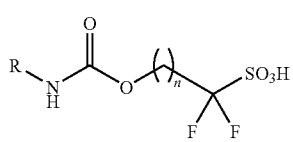
(2)

where n indicates an integer of 1 to 10; and R indicates a substituted or unsubstituted $C_1$-$C_{20}$ linear, branched or cyclic alkyl group, a substituted or unsubstituted $C_1$-$C_{20}$ linear, branched or cyclic alkenyl group, a substituted or unsubstituted $C_6$-$C_{15}$ aryl group, or a $C_4$-$C_{15}$ heteroaryl group, the method comprising: irradiating the photoacid generator according to claim 6 with a high-energy radiation selected from an ultraviolet ray, a far-ultraviolet ray, an extreme-ultraviolet ray, an electron beam, an X-ray, an excimer laser, a γ-ray and a synchrotron radiation.

9. A resist material comprising a base resin, the photoacid generator according to claim 6 and a solvent.

10. The resist material according to claim 9, wherein the base resin is either a polymer of one kind of monomer, or a copolymer of two or more kinds of monomers, selected from the group consisting of olefins, fluoroolefins, acrylic esters, methacrylic esters, fluorine-containing acrylic esters fluorine-containing methacrylic esters, norbornene compounds, fluorine-containing norbornene compounds, styrenic compounds, fluorine-containing styrenic compounds, vinyl ethers and fluorine-containing vinyl ethers.

11. The resist material according to claim 9, wherein the base resin is a polymer compound having a repeating unit represented by the following general formula (6)

(6)

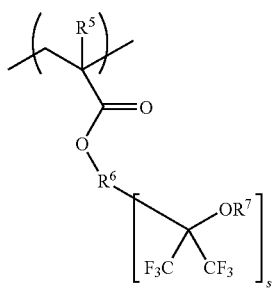

where $R^5$ indicates a hydrogen atom, a halogen atom, a hydrocarbon group or a fluoroalkyl group; $R^6$ indicates a linear or branched alkyl group, an alkyl group having a ring structure, an aromatic ring, or a composite group thereof, and may partially be fluorinated; $R^7$ indicates a hydrogen atom, a hydrocarbon group that may be branched, a fluoroalkyl group, or a cyclic group having an aromatic structure or aliphatic ring structure, and may contain an oxygen or carbonyl bond; and s indicates an integer of 1 to 2.

12. The resist material according to claim 11, wherein the repeating unit of the base resin is represented by the following general formula (7)

(7)

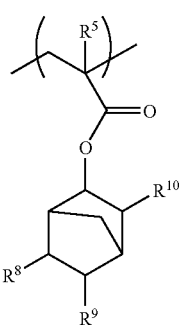

where $R^5$ indicates a hydrogen atom, a halogen atom, a hydrocarbon group, or a $C_1$-$C_3$ alkyl or fluoroalkyl group; either one of $R^8$, $R^9$ and $R^{10}$ indicates a $CF_3C(CF_3)(OH)CH_2$— group and the other two of $R^8$, $R^9$ and $R^{10}$ indicate hydrogen atoms.

13. The resist material according to claim 11, wherein the repeating unit of the base resin is represented by the following general formula (8)

(8)

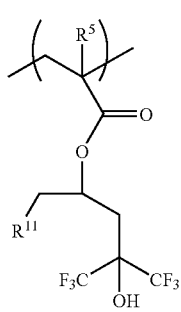

where $R^5$ indicates a hydrogen atom, a halogen atom, a hydrocarbon group or a fluoroalkyl group; and $R^{11}$ indicates a hydrogen atom, a methyl group, an ethyl group, a n-propyl group, an isopropyl group, a n-butyl group, a sec-butyl group, a tert-butyl group, a fluoromethyl group, a difluoromethyl group, a trifluoromethyl group or a perfluoroethyl group.

14. The resist material according to claim 11, wherein the repeating unit of the base resin is represented by the following general formula (9)

(9)

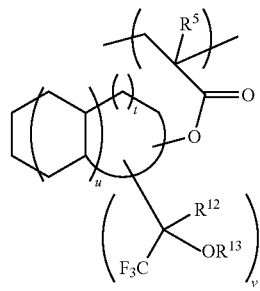

where $R^5$ indicates a hydrogen atom, a halogen atom, a hydrocarbon group or a fluoroalkyl group; $R^{12}$ indicates a methyl group or a trifluoromethyl group; $R^{13}$ indicates a hydrogen atom, a $C_1$-$C_{25}$ linear or $C_3$-$C_{25}$ branched or cyclic hydrocarbon group, or a $C_6$-$C_{26}$ aromatic hydrocarbon group, a part of which may contain a fluorine atom, an oxygen atom or a carbonyl bond; u indicates an arbitrary integer of 0 to 2; t and v each independently indicate an arbitrary integer of 1 to 8 and satisfy a relationship of $v \leq t+2$; and, when there are a plurality of $R^{12}$ and $R^{13}$, they may be the same or different.

15. The resist material according to claim 9, wherein the base resin contains a repeating unit represented by the following general formula (10)

(10)

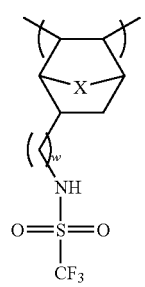

where X indicates either —$CH_2$—, —O— or —S—; and w indicates an integer of 2 to 6.

16. The resist material according to claim 9, wherein the base resin contains a repeating unit represented by the following general formula (11)

(11)

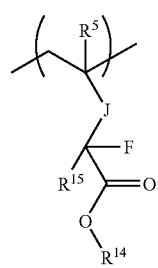

where $R^5$ indicates a hydrogen atom, a halogen atom, a hydrocarbon group or a fluoroalkyl group; $R^{15}$ indicates a fluorine atom or a fluoroalkyl group; J indicates a divalent linking group; and $R^{14}$ indicates an acid-labile protecting group represented by either one of the following general formulas (d) to (h)

$$R^{16}\text{—O—C(=O)—} \quad (d)$$

where $R^{16}$ indicates a $C_1$-$C_4$ alkyl group that may have a substituent, a $C_3$-$C_{30}$ alicyclic hydrocarbon group that may have a substituent, or a $C_6$-$C_{14}$ aryl group that may have a substituent $$R^{16}\text{—O—CHR}^{17}\text{—} \quad (e)$$

where $R^{16}$ is the same as defined in the general formula (d); $R^{17}$ indicates a hydrogen atom, a $C_1$-$C_4$ alkyl group that may have a substituent, a $C_3$-$C_{30}$ alicyclic hydrocarbon group that may have a substituent, a $C_1$-$C_6$ alkoxy group that may have a substituent, a $C_2$-$C_4$ alkenyl group that may have a substituent, a $C_6$-$C_{14}$ aryl group that may have a substituent, or a $C_7$-$C_{20}$ aralkyl group that may have a substituent $$CR^{18}R^{19}R^{20}\text{—} \quad (f)$$

where $R^{18}$, $R^{19}$ and $R^{20}$ may be the same or different and each independently indicate a $C_1$-$C_4$ alkyl group that may have a substituent, a $C_3$-$C_{30}$ alicyclic hydrocarbon group that may have a substituent, a $C_2$-$C_4$ alkenyl group that may have a substituent, a $C_6$-$C_{14}$ aryl group that may have a substituent, or a $C_7$-$C_{20}$ aralkyl group that may have a substituent; and two of $R^{18}$, $R^{19}$ and $R^{20}$ may be bonded to each other to form a ring structure $$SiR^{18}R^{19}R^{20}\text{—} \quad (g)$$

where $R^{18}$, $R^{19}$ and $R^{20}$ are the same as defined in the general formula (f)

$$R^{16}\text{—C(=O)—} \quad (h)$$

where $R^{16}$ is the same as defined in the general formula (d).

17. The resist material according to claim 9, wherein the resist material is a chemically amplified positive type resist material in which the base resin is insoluble or difficult to dissolve in a developer and is made soluble in the developer by the action of an acid.

18. A pattern formation method, comprising:
applying the resist material according to any one of claim 9 to a substrate;
after heat treating the applied resist material, exposing the applied resist material to a high-energy radiation of 300 nm or less wavelength through a photomask; and
after heat treating the exposed resist material as needed, developing the exposed resist material with a developer.

19. The pattern formation method according to claim 18, wherein the pattern formation method is immersion lithography using an ArF excimer laser of 193 nm wavelength as the high energy radiation and allowing insertion of water or a liquid of higher refractive index than that of the air between the substrate and projector lens.

20. Triphenylsulfonium cyclohexylcarbamic acid-2,2-difluoroethylsulfonate represented by the following formula

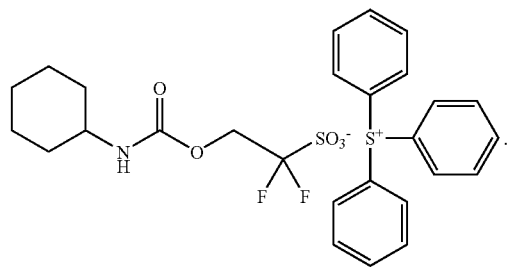

21. Triphenylsulfonium adamantane-1-yl-carbamic acid-2,2-difluoroethylsulfonate represented by the following formula

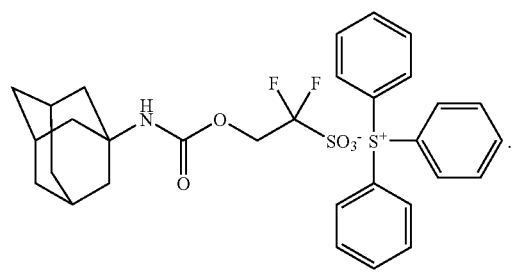

* * * * *